United States Patent
Ajito et al.

(10) Patent No.: US 6,750,219 B1
(45) Date of Patent: Jun. 15, 2004

(54) Ω-AMINO-α-HYDROXYCARBOXYLIC ACID DERIVATIVES HAVING INTEGRIN $\alpha_v\beta_3$ ANTAGONISTIC ACTIVITY

(75) Inventors: Keiichi Ajito, Yokohama (JP); Naokazu Yahata, Yokohama (JP); Minoru Ishikawa, Yokohama (JP); Dai Kubota, Yokohama (JP); Shoichi Murakami, Yokohama (JP); Mikio Yamamoto, Yokohama (JP); Kazuyuki Fujishima, Yokohama (JP); Shuichi Gomi, Yokohama (JP); Shokichi Ouchi, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 10/048,914
(22) PCT Filed: Aug. 2, 2000
(86) PCT No.: PCT/JP00/05177
§ 371 (c)(1), (2), (4) Date: Feb. 5, 2002
(87) PCT Pub. No.: WO01/10844
PCT Pub. Date: Feb. 15, 2001

(30) Foreign Application Priority Data
Aug. 5, 1999 (JP) .......................................... 11-222098

(51) Int. Cl.[7] .................... C07D 403/04; C07D 403/12; C07D 211/98; A61K 31/4523; A61P 9/10
(52) U.S. Cl. ........................ 514/256; 546/210; 546/215; 546/216; 546/223; 546/235; 544/332; 544/335; 514/269; 514/275; 514/326; 514/327; 514/331
(58) Field of Search ................................. 546/210, 215, 546/216, 223, 235; 544/332, 335; 514/269, 275, 256, 326, 327, 331

(56) References Cited

U.S. PATENT DOCUMENTS

| | | | |
|---|---|---|---|
| 5,843,906 A | 12/1998 | Chandrakumar et al. | 514/19 |
| 5,852,210 A | 12/1998 | Chen et al. | 562/439 |

FOREIGN PATENT DOCUMENTS

| | | |
|---|---|---|
| EP | 468766 | 1/1992 |
| EP | 796855 | 9/1997 |
| EP | 820988 | 1/1998 |
| EP | 820991 | 1/1998 |
| EP | 853084 | 7/1998 |
| GB | 2327609 | 2/1999 |
| GB | 2327672 | 2/1999 |
| JP | 5-97818 | 4/1993 |
| WO | 94/21599 | 9/1994 |
| WO | 95/32710 | 12/1995 |
| WO | 96/37492 | 11/1996 |
| WO | 97/01540 | 1/1997 |
| WO | 97/08145 | 3/1997 |
| WO | 97/23451 | 7/1997 |
| WO | 97/23480 | 7/1997 |
| WO | 97/24119 | 7/1997 |
| WO | 97/24336 | 7/1997 |
| WO | 97/26250 | 7/1997 |
| WO | 97/33887 | 9/1997 |
| WO | 97/36858 | 10/1997 |
| WO | 97/36859 | 10/1997 |
| WO | 97/36860 | 10/1997 |
| WO | 97/36861 | 10/1997 |
| WO | 97/36862 | 10/1997 |
| WO | 97/37655 | 10/1997 |
| WO | 98/08840 | 3/1998 |
| WO | 98/18460 | 5/1998 |
| WO | 98/25892 | 6/1998 |
| WO | 98/30542 | 7/1998 |
| WO | 98/31359 | 7/1998 |
| WO | 98/35949 | 8/1998 |
| WO | 98/43962 | 10/1998 |
| WO | 98/46220 | 10/1998 |
| WO | 99/05107 | 2/1999 |
| WO | 99/38849 | 8/1999 |
| WO | 99/50249 | 10/1999 |
| WO | 99/52872 | 10/1999 |

OTHER PUBLICATIONS

R. I. Souhami and J. Moxham ed.; "Textbook of Medicine" (Oct. 2002, Churchill Livingston, UK), see Chapter 4 p. 79–104.*

(List continued on next page.)

Primary Examiner—Mark L. Berch
Assistant Examiner—Kahsay Habte
(74) Attorney, Agent, or Firm—Wenderoth, Lind & Ponack, L.L.P.

(57) ABSTRACT

An objective of the present invention is to provide highly water-soluble compounds having integrin $\alpha_v\beta_3$ antagonistic activity. The compounds according to the present invention are compounds represented by formula (I) and pharmaceutically acceptable salts or solvates thereof:

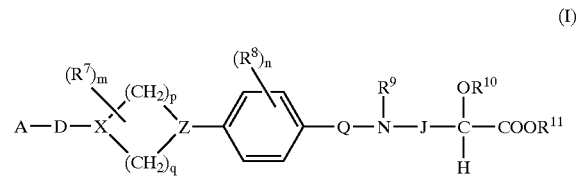

wherein A represents a two nitrogen atom-containing optionally substituted saturated or unsaturated five- to seven-membered heterocyclic group, which is optionally condensed with another carbocyclic ring or heterocyclic ring to form a bicyclic group, or —C(—NR$^1$R$^2$)(=NR$^3$) wherein R$^1$, R$^2$, and R$^3$ represent hydrogen, alkyl or the like; D represents a bond, >NR$^4$, wherein R$^4$ represents hydrogen or optionally substituted alkyl, —O—, or —S—; X and Z represent either CH or N; R$^7$ and R$^8$ represent C$_{1-6}$ alkyl, halogen, oxygen or the like; Q represents >C=O, >CHR$^{13}$ or >CHOR$^{13}$ wherein R$^{13}$ represents hydrogen or alkyl; R$^9$ represents hydrogen, alkyl or the like; J represents a bond or alkylene having 1 to 3 carbon atoms; R$^{10}$ and R$^{11}$ represent hydrogen, alkyl or the like; m is an integer of 0 to 5; n is an integer of 0 to 4; and p and q are an integer of 1 to 3.

17 Claims, No Drawings

OTHER PUBLICATIONS

Chalmers (TiPS vol. 17, pp. 166–172 Apr. 1996).*
NATURE vol. 407 Sep. 14, 2000, pp. 249–257.*
19th Symposium on Medicinal Chemistry, 8th Annual Meeting of Division of Medicinal Chemistry, Abstracts, The Pharmaceutical Society of Japan Division of Medicinal Chemistry, Tokyo, Nov. 17–19, 1999, pp. 49–50.
American Chemical Society Division of Medicinal Chemistry, Abstracts, 218th ACS National Meeting New Orleans, LA, Aug. 22–26, 1999, paper 63.
M.R. Keeman et al., Bioorganic & Medicinal Chemistry Letters, vol. 8, No. 22, pp. 3165–3170 (1998).
M.R. Keeman et al., Journal of Medicinal Chemistry, vol. 40, No. 15, pp. 2289–2292 (1997).
Hynes et al., Cell, vol. 69, pp. 11:25, (1992).
Takagi et al., The 50th Annual Meeting of the Japan Society for Cell Biology, S5-1, (1997).
Springer, Proc. Natl. Acad. Sci. USA, vol. 94, pp. 65–72, (1997).
Irie et al., The 50th Annual Meeting of the Japan Society for Cell Biology, S5-2, (1997).
Oxvig et al., Proc. Natl. Acad. Sci. USA, vol. 95, pp. 4870–4875, (1998).
Brooks, DN&P, vol. 10, No. 8, pp. 456–461, (1997).
Okada et al., American Journal of Pathology, vol. 149, No. 1, pp. 37–44, (1996).
S. Srivatsa et al., The 69th Annual Meeting Of The American Heart Association, 0231, (1996).
Gourvest et al., The 18th Annual Meeting Of the American Society for Bone and Mineral Research, p. 228, (1996).
Rodan et al., The 18th Annual Meeting of The American Society for Bone and Mineral Research, M430, (1996).
Yue et al., The 70th Annual Meeting of American Heart Association, 3733, (1997).
Racanelli et al., The 70th Annual Meeting of American Heart Association, 3734, (1997).
Friedlander et al., Conference of American IBC, The Scripps Research Institute, (Sep. 11, 1997).
Westlin, Conference of American IBC, (Feb. 23, 1998).
Lark et al., The 2nd Joint Conference of the American Society for Bone and Mineral Research and Intenational Bone and Mineral Society, T064, (1998).
Keenan et al., Bioorganic & Medicinal Chemistry Letters 8, pp. 3171–3176, (1998).
Carron et al., Cancer Research, 58, pp. 1930–1935, (1998).
Miller et al., Bioorganic & Medicinal Chemistry Letters 9, pp. 1807–1812, (1999).
Choi et al., Journal of Vascular Surgery, 19, pp. 125–134 (1994).
Matsuno et al., Circulation, vol. 90, No. 5, pp. 2203–2206, (1994).
Storgard et al., The Journal of Clinical Investigation, vol. 103, No. 1, pp. 47–54, (1999).
Tran et al., Bioorganic & Medicinal Chemistry Letters, vol. 7, No. 8, pp. 997–1002, (1997).
Ojima et al., Journal of the Society of Synthetic Organic Chemistry, 52, pp. 413–425, (1994).
Furuya, Shin–Tanpakushitu Oyo Kogaku, Fujitec Corporation, pp. 895–901.
Hirschmann et al., J. Am. Chem. Soc., vol. 115, pp. 12550–12568, (1993).
Nicolaou et al., Tetrahedron, vol. 53, No. 26, pp. 8751–8778, (1997).
Keenan et al., Journal of Medicinal Chemistry, vol. 40, No. 15, pp. 2289–2292, (1997).
Corbett et al., Bioorganic & Medicinal Chemistry Letters, vol. 7, No. 11, pp. 1371–1376 (1997).
Nicolaou et al, Bioorganic & Medicinal Chemistry 6, pp. 1185–1208 (1998).
Keenan et al., Bioorganic & Medicinal Chemistry Letters 8, pp. 3165–3170 (1998).
Rockwell et al., Bioorganic & Medicinal Chemistry Letters 9, pp. 937–942 (1999).
Keenan et al., Bioorganic & Medicinal Chemisry Letters 9, pp. 1801–1806 (1999).
Perreault et al., Tetrahedron, vol. 51, No. 2, pp. 353–362, (1995).
Kouns et al., Blood, vol. 80, No. 10, pp. 2539–2547, (1992).
Pytela et al., Methods in Enzymology, vol. 144, pp. 475–489 (1987).
Kikugawa et al., Chem. Pharm. Bull., vol. 25, No. 10, pp. 2624–2637 (1977).
Okada et al., Vascular Biology, vol. 29, No. 11, pp. 2753–2758 (1997).

* cited by examiner

Ω-AMINO-α-HYDROXYCARBOXYLIC ACID DERIVATIVES HAVING INTEGRIN $\alpha_v\beta_3$ ANTAGONISTIC ACTIVITY This application is a U.S. national stage of International Application No. PCT/JP00/05177 filed Aug. 2, 2000.

BACKGROUND OF THE INVENTION

1. Field of the Invention

The present invention relates to novel ω-amino-α-hydroxycarboxylic acid derivatives having integrin $\alpha_v\beta_3$ antagonistic activity and a pharmaceutical composition comprising as active ingredient at least one of said derivatives.

2. Description of Related Art

A signal transmission system is very important to organisms from the viewpoints of physiological significance, the regulation of gene expression and the like. It has been clarified that integrins, i.e., glycoprotein receptors which are involved in cell adhesion and penetrate cell membranes, are related, for example, to wound healing and hemostasis, phagocytosis, biophylaxis, and the construction of cytoskeletons and, in addition, as such are signal transfer molecules (Cell, 69, 11, (1992)). For this reason, in recent years, organic chemistry associated with integrins has suddenly become drawn attention from the viewpoint of pharmacology, as well as from the viewpoints of molecular biology and cell biology.

It is being elucidated that, while the conformation of integrins undergoes a dynamic and complicate change, integrins binds to various ligands to transmit signal in both intracellular and extracellular directions (Junichi Takagi et al., The 50th Annual Meeting of the Japan Society for Cell Biology, S5-1, 1997). T. A. Springer of Harvard Medical School has recently predicted that a certain activated integrin has a β-propeller structure and binds to a ligand on the upper face of the β-propeller (Proc. Natl. Acad. Sci. USA, 94, 65, 1997). This hypothesis was also supported by researchers in Japan (Atsushi Irie et al., The 50th Annual Meeting of the Japan Society for Cell Biology, S5-2, 1997), and three-dimensional analysis on a molecular level associated with the activation of integrins as well as binding between integrins and ligands and the like has been initiated in real earnest.

T. A. Springer et al. has recently substantiated a hypothesis regarding the β-propeller domain by experimentation, and has suggested that the β-propeller domain in integrin α-subunit has important interaction with integrin β-subunit (Proc. Natl. Acad. Sci. USA, 95, 4870, 1998).

Among others, integrin $\alpha_v\beta_3$ binds to various extracellular matrixes, that is, ligands deeply involved, for example, in biodynamics or the crisis of diseases, such as vitronectin, fibrinogen, fibronectin, osteopontin, thrombospondin, von Willebrand factors, and collagen, to form complexes. Accordingly, integrin $\alpha_v\beta_3$ is of special interest as a potential drug target (DN & P, 10, 456, 1997). In fact, $\alpha_v\beta_3$ is expressed in a large amount in B cells, macrophages, monocytes, smooth muscle, activated endothelial cells and the like. Further, $\alpha_v\beta_3$ is known not to be strongly expressed in endothelial cells in a resting stage, but to be highly activated in the course of growth and infiltration, that is, in vascularization, wound healing, and inflamed sites. Further, the correlation between the frequency of expression of $\alpha_v\beta_3$ and the increase in infiltration of cancer has been observed in various cancer cells. On the other hand, a group of researchers at Scripps Research Institute in U.S.A. have clarified by advanced computer-assisted video imaging microscopy that microvascular expression of $\alpha_v\beta_3$ is observed during experimental middle cerebral artery occlusion and reperfusion in a baboon as a model (Y. Okada et al., Am. J. Pathol., 149, 37, 1996).

As described above, relationship of cell species, which express integrin $\alpha_v\beta_3$ in vivo, with $\alpha_v\beta_3$ activation stage, biophylaxis mechanism and the like has led to an expectation of clinical application of molecules having integrin $\alpha_v\beta_3$ antagonistic activity in various fields. In fact, compounds having integrin $\alpha_v\beta_3$ antagonistic activity are intended to be used clinically, and the results of animal tests on compounds having $\alpha_v\beta_3$ antagonistic activity in a wide range of diseases have been reported (S. S. Srivatsa et al., The 69th Annual Meeting of American Heart Association, 0231, 1996 (DuPont-Merc); J. F. Gourvest et al., The 18th Annual Meeting of The American Society for Bone and Mineral Research, p228, 1996 (Roussel-Hoechst); S. B. Rodan et al., The 18th Annual Meeting of The American Society for Bone and Mineral Research, M430, 1996 (Merck); T. L. Yue et al., The 70th Annual Meeting of American Heart Association, 3733, 1997 (SmithKline Beecham); A. L. Racanelli et al., The 70th Annual Meeting of American Heart Association, 3734, 1997 (DuPont-Merc); M. Friedlander et al., Conference of American IBC, Sep. 11, 1997 (The Scripps Research Institute); W. S. Westlin, Conference of American IBC, Feb. 23, 1998 (Searle); M. W. Lark et al., The 2nd Joint Conference of The American Society for Bone and Mineral Research and International Bone and Mineral Society, T064, 1998 (SmithKline Beecham); R. K. Keenan et al., Bioorg. Med. Chem. Lett., 8, 3171, 1998 (SmithKline Beecham); C. P. Carron et al., Cancer Res., 58, 1930, 1998 (Searle); and W. H. Miller et al., Bioorg. Med. Chem. Lett., 9, 1807, 1999 (SmithKline Beecham)).

From the viewpoint of chemical structure, compounds having integrin $\alpha_v\beta_3$ antagonistic activity can be classified into antibodies, low-molecular peptide and compounds analogous thereto, and low-molecular organic compounds. All the antagonists are structurally related to the sequence of tripeptide RGD (arginine-glycine-aspartic acid) that are considered indispensable for recognition in the attachment of a ligand. Low-molecular peptides having antagonistic activity include disintegrins derived from venom of snakes and, in addition, cyclic peptides. One of them, GpenGRGDSPCA, has been reported to inhibit migration of smooth muscle and to block integrin $\alpha_v\beta_3$, thereby to actually inhibit neointima formation in rabbits (E. T. Choi et al., J. Vasc. Surg., 19, 125, 1994). Further, RGD-containing cyclic peptide G4120 inhibited neointima formation in hamsters (Circulation, 90, 2203 (1994)). Further, Scripps Research Institute has recently reported that cyclic peptides having $\alpha_v\beta_3$ antagonistic activity are promising novel therapeutic agents for rheumatic arthritis (C. M. Storgard et al., J. Clin. Invest., 103, 47 (1999)). On the other hand, cyclic peptides containing BTD designed by a β-turn mimic have been proved to strongly bind to $\alpha_v\beta_3$ receptors (M. Goodman et al., Bioorg. Med. Chem. Lett., 7, 997, 1997).

Several methods are known for designing small molecules through the utilization of the amino acid sequence of interest (RGD being used here) as a clue (Gen Ojima et al., Journal of The Society of Synthetic Organic Chemistry, 52, 413 (1994); Toshio Furuya, Shin-Tanpakushitu Oyo Kogaku, Fujitec Corporation). A peptide mimesis for constructing a new molecule based on the backbone of a peptide chain is generally known in the art. The concept of a new de novo design focused on the chemical structure and spatial configuration of amino acid side chains has been introduced for the first time early in the 1990s (R. Hirschman et al., J. Am. Chem. Soc., 115, 12550 (1993)). An attempt to apply this approach to the design and synthesis of $\alpha_v\beta_3$ antagonists has already been initiated (K. C. Nicolaou et al., Tetrahedron, 53, 8751, 1997).

Up to now, small molecules having $\alpha_v\beta_3$ antagonistic activity are disclosed in WO 95/32710 (Merck); WO 96/37492 (Dupont-Merc); WO 97/01540 (SmithKline Beecham); WO 97/08145 (Searle Co.); WO 97/23451 (Merck); WO 97/23480 (Dupont-Merc); WO 97/24119 (SKB); WO 97/26250 (Merck); WO 97/33887 (Dupont-Merc); WO 97/36858 (Searle); WO 97/36859 (Searle); WO 97/36860 (Searle); WO 97/36861 (Searle); WO 97/36862 (Searle); WO 97/24336 (SmithKline Beecham); WO 97/37655 (Merck); WO 98/08840 (Merck); WO 98/18460 (Merck); WO 98/25892 (Lilly); WO 98/30542 (SmithKline Beecham); WO 98/31359 (Merck); WO 98/35949 (Merck); WO 98/43962 (Dupont-Merc); WO 98/46220 (Merck); WO 99/05107 (SmithKline Beecham); U.S. Pat. No. 5,843,906 (Searle); U.S. Pat. No. 5,852,210 (Searle); EP 796855 (Hoechst); EP 820988 (Hoechst); EP 820991 (Hoechst); EP 853084 (Hoechst); GB 2326609 (Merck); GB 2327672 (Merck); R. M. Keenan et al., J. Med. Chem., 40, 2289 (1997); J. W. Corbett et al., Bioorg. Med. Chem. Lett., 7, 1371 (1997); K. C. Nicolaou et al., Bioorg. Med. Chem., 6, 1185 (1998); R. M. Keenan, et al., Bioorg. Med. Chem. Lett., 8, 3165 (1998); A. R. Rockwell et al. Bioorg. Med. Chem. Lett., 9, 937 (1999); and R. M. Keenan et al., Bioorg. Med. Chem. Lett., 9, 1801 (1999).

However, low-molecular integrin $\alpha_v\beta_3$ antagonists having a hydroxyl group at the $\alpha$-position of the carboxylic acid have not yet been reported.

SUMMARY OF THE INVENTION

The present inventors have found that a certain group of derivatives have potent integrin $\alpha_v\beta_3$ antagonistic activity. The present inventors have also found that a certain group of derivatives have potent GP IIb/IIIa antagonistic activity and human platelet aggregation inhibitory activity. The present inventors have further found that these derivatives have excellent water solubility and do not substantially have pharmacological activity which is not involved in integrin $\alpha_v\beta_3$ directly.

Accordingly, an object of the present invention is to provide a compound having integrin $\alpha_v\beta_3$ antagonistic activity, GP IIb/IIIa antagonistic activity, and/or human platelet aggregation inhibitory activity and also having excellent water solubility.

Another object of the present invention is to provide a therapeutic agent for a disease selected from the group consisting of integrin $\alpha_v\beta_3$-mediated diseases and diseases where GP IIb/IIIa antagonistic activity and/or platelet aggregation inhibitory activity are therapeutically effective, and an agent for inhibiting platelet aggregation.

According to one aspect of the present invention, there is provided a compound represented by formula (I) or a pharmaceutically acceptable salt or solvate thereof:

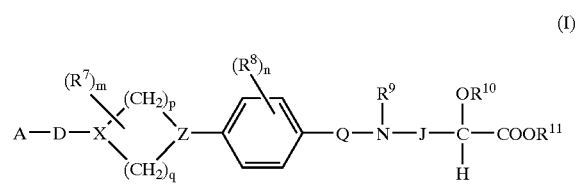

(I)

wherein
A represents a saturated or unsaturated five- to seven-membered heterocyclic group containing two nitrogen atoms, which is optionally condensed with another saturated or unsaturated five- to seven-membered carbocyclic ring or heterocyclic ring to form a bicyclic group, wherein the heterocyclic group and the bicyclic group are optionally substituted by $C_{1-6}$ alkyl, amino, $C_{1-6}$ alkoxy, $C_{1-6}$ alkoxycarbonyl, or aralkyl and the $C_{1-6}$ alkyl, amino, $C_{1-6}$ alkoxy, $C_{1-6}$ alkoxycarbonyl, and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom,
or a group represented by formula

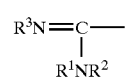

wherein
$R^1$, $R^2$, and $R^3$, which may be the same or different, represent a hydrogen atom, $C_{1-6}$ alkyl, $C_{2-6}$ alkenyl, $C_{2-6}$ alkynyl, aralkyl, or nitrile, or $R^1$ and $R^2$ may together form group —$(CH_2)_i$—, wherein i is 4 or 5, or group —$(CH_2)_2$—O—$(CH_2)_2$—, and the $C_{1-6}$ alkyl, $C_{2-6}$ alkenyl, $C_{2-6}$ alkynyl, and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom;
D represents a bond; >$NR^4$ wherein $R^4$ represents a hydrogen atom or $C_{1-6}$ alkyl and this alkyl group is optionally substituted by phenyl optionally substituted by $C_{1-6}$ alkoxy, $C_{1-6}$ alkyl, $C_{1-6}$ alkoxy, $C_{1-6}$ alkoxycarbonyl, aralkyl, amino, hydroxyl, or a halogen atom; >$CR^5R^6$ wherein $R^5$ and $R^6$ each independently represent a hydrogen atom or $C_{1-6}$ alkyl and this alkyl group is optionally substituted by phenyl optionally substituted by $C_{1-6}$ alkoxy, $C_{1-6}$ alkyl, $C_{1-6}$ alkoxy, $C_{1-6}$ alkoxycarbonyl, aralkyl, amino, hydroxyl, or a halogen atom; —O—; or —S—;
X and Z, which may be the same or different, represent CH or N;
$R^7$ represents $C_{1-6}$ alkyl, $C_{1-6}$ alkoxy, a halogen atom, amino, nitro, hydroxyl, an oxygen atom, or cyano and the $C_{1-6}$ alkyl and $C_{1-6}$ alkoxy groups are optionally substituted by $C_{1-6}$ alkyl, $C_{1-6}$ alkoxy, $C_{1-6}$ alkoxycarbonyl, aralkyl, amino, hydroxyl, or a halogen atom;
$R^8$ represents $C_{1-6}$ alkyl, $C_{1-6}$ alkoxy, a halogen atom, amino optionally substituted by one or two $C_{1-6}$ alkyl groups, nitro, hydroxyl, an oxygen atom, or cyano and the $C_{1-6}$ alkyl and $C_{1-6}$ alkoxy groups are optionally substituted by $C_{1-6}$ alkyl, $C_{1-6}$ alkoxy, $C_{1-6}$ alkoxycarbonyl, aralkyl, amino, hydroxyl, or a halogen atom;
Q represents >C=O, >$CHR^{13}$, or >$CHOR^{13}$ wherein $R^{13}$ represents a hydrogen atom or $C_{1-6}$ alkyl;

$R^9$ represents a hydrogen atom, $C_{1-6}$ alkyl, $C_{2-6}$ alkenyl, $C_{2-6}$ alkynyl, or aralkyl and the $C_{1-6}$ alkyl, $C_{2-6}$ alkenyl, $C_{2-6}$ alkynyl, and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom;

J represents a bond or alkylene having 1 to 3 carbon atoms wherein alkylene is optionally substituted by $C_{1-6}$ alkyl, $C_{1-6}$ alkoxy, $C_{1-6}$ alkoxycarbonyl, aralkyl, amino, hydroxyl, or a halogen atom;

$R^{10}$ represents a hydrogen atom, $C_{1-6}$ alkyl, $C_{2-6}$ alkenyl, $C_{2-6}$ alkynyl, aralkyl, or acyl and the $C_{1-6}$ alkyl, $C_{2-6}$ alkenyl, $C_{2-6}$ alkynyl, aralkyl, and acyl groups are optionally substituted by $C_{1-6}$ alkyl, $C_{1-6}$ alkoxy, $C_{1-6}$ alkoxycarbonyl, aralkyl, amino, hydroxyl, or a halogen atom;

$R^{11}$ represents a hydrogen atom, $C_{1-6}$ alkyl, or aralkyl and the $C_{1-6}$ alkyl and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom;

m is an integer of 0 to 5;

n is an integer of 0 to 4;

p is an integer of 1 to 3; and q is an integer of 1 to 3.

The compounds according to the present invention are useful as therapeutic agents for integrin $\alpha_v\beta_3$-mediated diseases.

DETAILED DESCRIPTION OF THE INVENTION

Compound

The terms "$C_{1-6}$ alkyl" and "$C_{1-6}$ alkoxy" as used herein as a group or a part of a group mean straight chain, branched chain, or cyclic alkyl and alkoxy having 1 to 6, preferably 1 to 4 carbon atoms.

The terms "$C_{2-6}$ alkenyl" and "$C_{2-6}$ alkynyl" as used herein as a group or a part of a group mean straight chain, branched chain, or cyclic alkenyl and alkynyl having 2 to 6, preferably 2 to 4 carbon atoms.

Examples of $C_{1-6}$ alkyl include methyl, ethyl, n-propyl, isopropyl, cyclopropyl, cyclopropylmethyl, n-butyl, i-butyl, s-butyl, t-butyl, n-pentyl, cyclopentyl, n-hexyl, and cyclohexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$ alkenyl include allyl.

Examples of $C_{2-6}$ alkynyl include 2-propynyl and ethynyl.

Examples of "saturated or unsaturated five- to seven-membered carbocyclic groups" include phenyl.

The term "saturated or unsaturated five- to seven-membered heterocyclic ring" as used herein means a five- to seven-membered heterocyclic ring containing at least one hetero-atom selected from oxygen, nitrogen, and sulfur atoms, preferably a five- to seven-membered heterocyclic ring containing one nitrogen atom, more preferably a five- or six-membered heterocyclic ring containing one nitrogen atom. The term "hetero-atom" used herein means an oxygen, nitrogen, or sulfur atom. Examples of saturated or unsaturated five- to seven-membered heterocyclic groups include pyrimidyl, 1,4,5,6-tetrahydropyrimidyl, imidazolyl, tetrahydro[1,3]diazepinyl, and imidazolidinyl.

The saturated heterocyclic group may be condensed with another saturated or unsaturated heterocyclic ring to form a bicyclic ring. Such condensed cyclic groups include benzimidazolyl, naphthyl, and azabenzimidazolyl, for example, imidazo[4,5-b]pyridyl.

The term "aralkyl" as used herein as a group or a part of a group means $C_{1-6}$ alkyl, preferably $C_{1-4}$ alkyl, substituted by a saturated or unsaturated five- to seven-membered carbocyclic group or heterocyclic group. Examples of aralkyl include benzyl and phenethyl.

The term "halogen atom" means a fluorine, chlorine, bromine, or iodine atom.

In preferred combinations of X with Z, X represents CH while Z represents N, or both X and Z represent N.

When D represents a bond, preferably, X represents N, and, more preferably, X represents N while Z represents N.

When D represents $>NR^4$, preferably, X represents CH, and, more preferably, X represents CH while Z represents N.

When D represents $>CR^5R^6$, preferably, x represents N, and, more preferably, X represents N while Z represents N.

When D represents —O—, preferably, X represents CH, and, more preferably, X represents CH while Z represents N.

When D represents —S—, preferably, X represents CH, and, more preferably, X represents CH while Z represents N.

D preferably represents a bond or $>NR^4$.

The bicyclic heterocyclic group represented by A is preferably a nine- or ten-membered heterocyclic group, more preferably a nine- or ten-membered heterocyclic group containing two or three nitrogen atoms.

Preferably, A represents a group of the following formula:

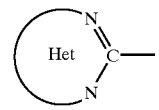

wherein

Het represents a saturated or unsaturated five- to seven-membered heterocyclic group containing two nitrogen atoms, which is optionally condensed with another saturated or unsaturated five- to seven-membered carbocyclic ring or heterocyclic ring to form a bicyclic group, wherein the heterocyclic group and the bicyclic group are optionally substituted by $C_{1-6}$ alkyl, amino, $C_{1-6}$ alkoxy, $C_{1-6}$ alkoxycarbonyl, or aralkyl and the $C_{1-6}$ alkyl, amino, $C_{1-6}$ alkoxy, $C_{1-6}$ alkoxycarbonyl, and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom.

More preferably, A represents a group of the following formula:

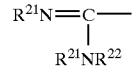

wherein $R^{21}$ and $R^{23}$, which may be the same or different, represent a hydrogen atom, $C_{1-6}$ alkyl, $C_{2-6}$ alkenyl, or aralkyl $R^{22}$ represents a hydrogen atom or $C_{1-6}$ alkyl, or $R^{21}$ and $R^{23}$ may together form group —$(CH_2)_4$—, group —$(CH_2)_3$—, group —$CHR^{24}CH_2CH_2$— wherein $R^{24}$ represents $C_{1-6}$ alkyl, a halogen atom, or amino, the alkyl group is optionally substituted by $C_{1-6}$ alkyl, $C_{1-6}$ alkoxy, $C_{1-6}$ alkoxycarbonyl, aralkyl, amino, hydroxyl, or a halogen atom and the amino group is optionally substituted by $C_{1-6}$ alkyl, $C_{1-6}$ alkoxy, $C_{1-6}$ alkoxycarbonyl, or aralkyl, group —CH$_2$CHR$^{24}$CH$_2$— wherein R$^{24}$ is as defined above,
group —CH$_2$CH$_2$—,
group —CHR$^{24}$CH$_2$— wherein R$^{24}$ is as defined above,
group —CR$^{25}$=CR$^{26}$— wherein R$^{25}$ and R$^{26}$, which may be the same or different, represent a hydrogen atom or C$_{1-6}$ alkyl, or R$^{25}$ and R$^{26}$ may together form —CH=CH—CH=CH—, —CR$^{24}$=CH—CH=CH— wherein R$^{24}$ is as defined above, —CH=CR$^{24}$—CH=CH— wherein R$^{24}$ is as defined above, —N=CH—CH=CH—, or —CH=N—CH=CH—, or R$^{21}$ and R$^{23}$ may together form
=CH—CH=CH—,
=CR$^{24}$—CH=CH—,
=CH—CR$^{24}$=CH—,
=CH—CH=N—, or
=CH—N=CH—, and R$^{22}$ may represent a single bond between R$^{21}$ and the nitrogen atom attached to R$^{21}$.

In the compound represented by formula (I), one or more hydrogen atoms in the following portion may be substituted by R$^7$.

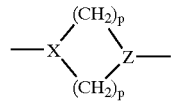

When m is zero (0), R$^7$ is absent. When m is 1, one hydrogen atom in the above portion is substituted by R$^7$. When m is 2 or more, two or more hydrogen atoms in the above portion are substituted by R$^7$. In this case, the substituents may be the same or different. When R$^7$ represents an oxygen atom, the bond between the R$^7$ and the above portion is a double bond. m is preferably an integer of 0 to 2.

In the compound represented by formula (I), one or more hydrogen atoms in the phenylene portion may be substituted by R$^8$.

When n is zero (0), R$^8$ is absent. When n is 1, one hydrogen atom in the phenylene portion is substituted by R$^8$. When n is 2 or more, two or more hydrogen atoms in the phenylene portion are substituted by R$^8$. In this case, the substituents may be the same or different. n is preferably an integer of 0 to 2.

Q preferably represents >C=O or >CH$_2$.

J preferably represents an optionally substituted methylene or ethylene chain.

R$^9$ preferably represents a hydrogen atom, C$_{1-6}$ alkyl (preferably methyl, propyl, or cyclopropylmethyl), or aralkyl (preferably benzyl or phenethyl).

R$^{10}$ preferably represents a hydrogen atom, C$_{1-6}$ alkyl, or acyl wherein C$_{1-6}$ alkyl and acyl are optionally substituted by C$_{1-6}$ alkyl, C$_{1-6}$ alkoxy, C$_{1-6}$ alkoxycarbonyl, aralkyl, amino, or hydroxyl.

R$^{11}$ preferably represents a hydrogen atom, unsubstituted C$_{1-6}$ alkyl, or unsubstituted aralkyl.

Preferred compounds represented by formula (I) are those wherein

A represents a group of formula

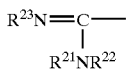

wherein
R$^{21}$, R$^{22}$, and R$^{23}$ are as defined above;
D represents a bond or >NR$^4$;
X represents N or CH;
Z represents N;
Q represents >C=O or >CH$_2$;
m and n are each an integer of 0 or 1;
R$^7$ represents optionally substituted C$_{1-6}$ alkyl, a halogen atom, or an oxygen atom;
R$^8$ represents a halogen atom, nitro, optionally substituted amino, cyano, optionally substituted C$_{1-6}$ alkyl, or optionally substituted C$_{1-6}$ alkoxy;
R$^9$ represents a hydrogen atom, optionally substituted C$_{1-6}$ alkyl, or optionally substituted aralkyl;
J represents an optionally substituted methylene or ethylene chain;
R$^{10}$ represents a hydrogen atom, optionally substituted C$_{1-6}$ alkyl, optionally substituted C$_{2-6}$ alkenyl, optionally substituted aralkyl, or optionally substituted acyl;
R$^{11}$ represents a hydrogen atom, optionally substituted C$_{1-6}$ alkyl, or optionally substituted aralkyl; and
p and q are each 1 or 2.

Further, preferred compounds represented by formula (I) are those wherein

A represents a group of formula

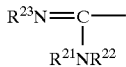

wherein
R$^{21}$ and R$^{23}$ both represent a hydrogen atom, or R$^{21}$ and R$^{23}$ together form
—CH$_2$CH$_2$CH$_2$CH$_2$—,
—CH$_2$CH$_2$CH$_2$—,
—CH$_2$CH$_2$—,
—CHR$^{24}$CH$_2$CH$_2$— wherein R$^{24}$ is as defined above,
—CH$_2$CHR$^{24}$CH$_2$— wherein R$^{24}$ is as defined above,
—CHR$^{24}$CH$_2$— wherein R$^{24}$ is as defined above, or
—CR$^{25}$=CR$^{26}$— wherein R$^{25}$ and R$^{26}$ both represent a hydrogen atom, or R$^{25}$ and R$^{26}$ together form —CH=CH—CH=CH—, —N=CH—CH=CH—, or —CH=N—CH=CH—;
R$^{22}$ represents a hydrogen atom or optionally substituted C$_{1-6}$ alkyl,
provided that, when R$^{21}$ and R$^{23}$ together form =CH—CH=CH—, =CR$^{24}$—CH=CH—, =CH—CR$^{24}$=CH—, =CH—CH=N—, or =CH—N=CH—, R$^{22}$ forms a bond;
D represents a bond or >NR$^4$;
X represents CH or N;
Z represents N;
m and n are each 0 or 1;
R$^7$ represents C$_{1-6}$ alkyl;
R$^8$ represents a halogen atom;
Q represents >C=O;
R$^9$ represents a hydrogen atom, optionally substituted C$_{1-6}$ alkyl, optionally substituted C$_{3-6}$ alkenyl, or optionally substituted aralkyl;

J represents an optionally substituted methylene or ethylene chain;

$R^{10}$ represents a hydrogen atom, optionally substituted $C_{1-6}$ alkyl, optionally substituted $C_{3-6}$ alkenyl, optionally substituted aralkyl, or optionally substituted acyl;

$R^{11}$ represents a hydrogen atom, optionally substituted $C_{1-6}$ alkyl, or optionally substituted aralkyl; and p and q are each 1 or 2.

Particularly preferred compounds represented by formula (I) are the following compounds:

t-butyl(2S)-hydroxy-3-[4-{4-(pyrimidin-2-yl)piperazin-1-yl}benzoylamino]propionate;
(2S)-hydroxy-3-[4-{4-(pyrimidin-2-yl)piperazin-1-yl}benzoylamino]propionic acid;
t-butyl(2S)-hydroxy-3-[4-{4-(pyrimidin-2-ylamino)piperidin-1-yl}benzoylamino]propionate;
t-butyl(2S)-t-butoxy-3-[4-{4-(pyrimidin-2-ylamino)piperidin-1-yl}benzoylamino]propionate;
(2S)-hydroxy-3-[4-{4-(pyrimidin-2-ylamino)piperidin-1-yl}benzoylamino]propionic acid;
(2S)-hydroxy-3-[4-{4-(1,4,5,6-tetrahydropyrimidin-2-ylamino)piperidin-1-yl}benzoylamino]propionic acid;
(2S)-acetoxy-3-[4-{4-(1,4,5,6-tetrahydropyrimidin-2-ylamino)piperidin-1-yl}benzoylamino]propionic acid;
t-butyl(2S)-t-butoxy-4-[4-{4-(pyrimidin-2-ylamino)piperidin-1-yl}benzoylamino]butyrate;
(2S)-hydroxy-4-[4-{4-(pyrimidin-2-ylamino)piperidin-1-yl}benzoylamino]butyric acid;
(2S)-hydroxy-4-[4-{4-(1,4,5,6-tetrahydropyrimidin-2-ylamino)piperidin-1-yl}benzoylamino]butyric acid;
benzhydryl 3-[3-fluoro-4-{4-(pyrimidin-2-ylamino)piperidin-1-yl}benzoylamino]-(2s)-hydroxypropionate;
t-butyl(2S)-t-butoxy-3-[3-fluoro-4-{4-(pyrimidin-2-ylamino)piperidin-1-yl}benzoylamino]propionate;
3-[3-fluoro-4-{4-(pyrimidin-2-ylamino)piperidin-1-yl}benzoylamino]-(2S)-hydroxypropionic acid; and
3-[3-fluoro-4-{4-(1,4,5,6-tetrahydropyrimidin-2-ylamino)piperidin-1-yl}benzoylamino]-(2S)-hydroxypropionic acid.

The compounds according to the present invention may form pharmacologically acceptable salts thereof. Such salts include non-toxic salts. Preferred salts include: hydrohalogenic acid salts such as hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, or maleic acid salts; amino acid salts such as glutamic acid salts or aspartic acid salts; alkali metal or alkaline earth metal salts such as sodium salts, potassium salts, and calcium salts; and organic alkali salts . such as pyridine salts or triethylamine salts.

The compounds according to the present invention may form solvates (for example, hydrates, alcoholates such as methanolate and ethanolate, and etherates such as tetrahydrofuran).

Production of Compounds

Compounds according to the present invention may be produced according to scheme 1. In the scheme, A, D, X, J, $R^7$, $R^8$, $R^9$, $R^{10}$, $R^{11}$, m, n, p, and q are as defined above.

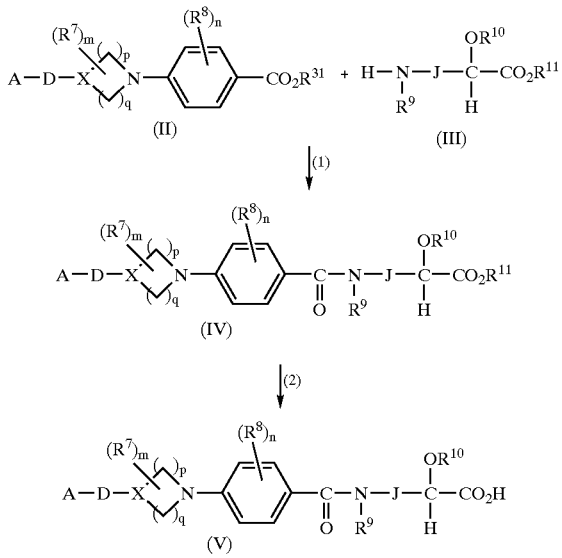

Scheme 1

A compound represented by formula (IV) can be prepared by hydrolyzing a carboxylic ester represented by formula (II), wherein $R^{31}$ represents $C_{1-6}$ alkyl or aralkyl, to give a compound represented by formula (II) wherein $R^{31}$ represents a hydrogen atom and then reacting the compound thus obtained with a compound represented by formula (III) to form an amide bond. Specifically, the compound represented by formula (IV) can be prepared by hydrolyzing the free carboxyl group in the compound represented by formula (II), wherein $R^{31}$ represents a hydrogen atom, with an alkali according to a conventional method and then reacting the compound thus obtained with the amine represented by formula (III) to perform condensation (step 1).

In the condensation reaction, a condensing agent, such as dicyclohexylcarbodiimide, diisopropylcarbodiimide, or 1-ethyl-3-(3-dimethylaminopropyl)carbodiimide hydrochloride, may be used either solely or in combination with N-hydroxysuccinimide, 1-hydroxybenzotriazole or the like. Benzotriazol-1-yloxytri(dimethylamino)phosphonium hexafluorophosphate may be used solely in the presence of a base. The combination of these reagents permits the desired condensation reaction to proceed with high efficiency. Preferably, from the viewpoint of optimizing the yield, 1 to 3 equivalents of 1-ethyl-3-(3-dimethylaminopropyl)carbodiimide hydrochloride or its free base is used in combination with 1 to 2 equivalents of 1-hydroxybenzotriazole, or alternatively, 1 to 2 equivalents of benzotriazol-1-yloxytri(dimethylamino)phosphonium hexafluorophosphate may be used.

Reaction solvents usable in the condensation reaction include dimethylformamide, dioxane, tetrahydrofuran, and methylene chloride. Preferred are dimethylformamide and a mixed solvent composed of dimethylformamide and methylene chloride. The reaction may be carried out in a range of 0 to 80° C., preferably in a range of 0 to 50° C.

In the condensation reaction, a tertiary amine, such as diisopropylethylamine, N-methylmorpholine, dimethylaminopyridine, or triethylamine, may be added as an organic base from the viewpoint of improving the yield. Preferably, 2 to 5 equivalents of N-methylmorpholine or diisopropylethylamine is added.

The reaction proceeds without the addition of these organic bases. The addition of the organic bases, however, is preferred from the viewpoint of the yield.

Compounds represented by formula (IV) wherein A represents an optionally substituted pyrimidine ring may be if necessary reduced to the corresponding tetrahydropyrimidine.

Compounds represented by formula (IV) wherein >C=O bonded to the phenylene portion is >CH$_2$ may be produced by reductively converting the carboxylic ester represented by formula (II), wherein R$^{31}$ represents C$_{1-6}$ alkyl or aralkyl, to an aldehyde and then reductively reacting the aldehyde thus obtained with the amine represented by formula (III). The reaction may be carried out according to the method described in Example 46 (a production example) of WO 99/52872.

Compounds represented by formula (IV) produced by the reductive amination wherein R$^9$ represents a group other than a hydrogen atom can also be produced by a reaction process other than the method described herein. Specifically, the above aldehyde may be reductively reacted with an amine of the following formula:

$$H_2N\text{—}J\text{—}CH(OR^{10})COOR^{11} \quad (III')$$

wherein R$^{10}$, R$^{11}$, and J are as defined in formula (I), to produce a compound represented by formula (V) wherein R$^9$ represents a hydrogen atom. Thereafter, this compound may be reductively aminated to introduce alkyl, alkenyl, or aralkyl into R$^9$. The introduction of alkyl, alkenyl, or aralkyl into R$^9$ is not always carried out for the compound represented by formula (IV) in the scheme. That is, the introduction of alkyl, alkenyl, or aralkyl into R$^9$ may be carried out for the compound represented by formula (V) in the scheme. The reaction may be carried out according to the method described in Example 49 of WO 99/52872.

Further, in this reaction, R$^{11}$ in —COOR$^{11}$ corresponding to the carboxylic ester portion in the amine may represent a hydrogen atom.

The amine represented by formula (III) used in step 1 may be generally synthesized from a commercially available conventional compound in a single or two steps. Specifically, the corresponding carboxylic ester can be prepared by treating ω-amino-α-hydoxycarboxylic acid with isobutene under proper reaction conditons, for example, in the presence of sulfuric acid. If necessary, the hydroxy group may be protected. Specifically, for example, 3-amino-(2S)-hydroxypropionic acid (L-isoserine) or 4-amino-(2S)-hydroxybutyric acid (AHBA) may be used as ω-amino-α-hydroxycarboxylic acid.

Protective groups of the carboxyl group include lower alkyl esters and aralkyl esters. For example, ethyl ester, t-butyl ester, and benzhydryl ester may be used.

In the esterification for the production of a t-butyl ester of 3-amino-(2S)-hydroxypropionic acid or 4-amino-(2S)-hydroxybutyric acid, a part of the hydroxyl group is sometimes t-butylated (etherified). In the condensation reaction in step 1, however, the hydroxyl group at the α-position may be protected or may not be protected.

In the t-butylation of 3-amino-(2S)-hydroxypropionic acid or 4-amino-(2S)-hydroxybutyric acid, when a conventional method described, for example, in WO 95/32710 as such is applied, the yield of the t-butylation can be improved, for example, by properly selecting the reaction solvent, the stirring efficiency, and the type and amount of the acid catalyst.

The esterification for the production of a benzhydryl ester of 3-amino-(2S)-hydroxypropionic acid or 4-amino-(2S)-hydroxybutyric acid proceeds without posing the problem of yield. In this case, when the amino group is previously converted to an acid salt, for example, a p-toluenesulfonic acid salt, the yield can be improved. The reaction solvent is not particularly limited. The reaction reagent is preferably diphenyldiazomethane.

Ester derivatives of 3-amino-(2S)-hydroxypropionic acid or 4-amino-(2S)-hydroxybutyric acid and hydroxyl-protected derivatives thereof, wherein R$^9$ represents a hydrogen atom, may be used in the condensation reaction in step 1. Alternatively, the amino group may be further modified followed by the use of the modified amino group in the condensation reaction. An example of chemical modification of the ω-amino group is alkylation. The alkylation may be carried out according to the method described in WO 99/38849 or WO 99/52872.

In step 2, the compound represented by formula (V) may be prepared by converting the carboxylic ester portion (—COOR$^{11}$) in the compound represented by formula (IV) to a free carboxyl group to produce, if necessary.

The carboxylic ester portion in the compound represented by formula (IV) may be converted to the contemplated free carboxyl group by a conventional method, for example, by hydrolysis with an alkali, hydrolysis with an acid, or reaction with an acid. The deesterification reaction may be achieved by a novel method without any restriction or limitation.

The compound represented by formula (IV) is orally administrable integrin α$_v$β$_3$ antagonist and/or GP IIb/IIIa antagonist. Therefore, the step of converting the carboxylic ester to the free carboxyl group is not always necessary.

Compounds represented by formula (V) wherein A represents an optionally substituted a pyrimidine ring may be, if necessary, reduced to the corresponding tetrahydropyrimidine. The reduction may be carried out by a conventional method. Examples of reduction methods usable herein include catalytic reduction in the presence of a catalyst, such as palladium-carbon, ruthenium-carbon, rhodium-carbon, palladium oxide, platinum oxide, ruthenium oxide, rhodium oxide, rhodium aluminum oxide complex, Raney nickel, or palladium black, and a reaction, for example, with metallic sodium or metallic lithium in liquid ammonia. Preferably, the reduction is carried out in an acidic solvent, for example, in acetic acid acidified with hydrochloric acid, in the presence of palladium-carbon with hydrogen under normal or applied pressure.

Compounds represented by formula (II) in scheme 1, wherein D represents >NR$^4$, may be produced by introducing group A into the free primary amine in the compound represented by formula (VI)

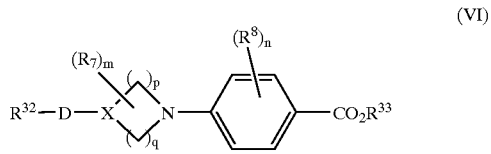

(VI)

wherein D represents >NR$^4$; R$^{32}$ represents a protective group of amino; R$^{33}$ represents C$_{1-6}$ alkyl or aralkyl; and X, R$^7$, R$^8$, p, and q are as defined above. The N—C bond between the compound represented by formula (VI) and the group A may be formed by reacting the compound represented by formula (VI) with a reagent, such as optionally modified or substituted 2-bromopyrimidine, modified or substituted 2-chlorobenzimidazole, or 2-methylthio-2-imidazoline, in the presence of a reaction solvent, such as dimethylformamide, dimethyl sulfoxide, sulfolane, pyridine, or methanol, preferably dimethylformamide, in a temperature range of 50 to 170° C., preferably in a temperature range of 60 to 140° C.

Reagents usable in this step is not limited to those recited herein, and any reagent may be used so far as a carbon atom attached to two nitrogen atoms finally combines with the nitrogen atom in the primary amine attached to a carbon atom in the piperidine derivative to form a single bond. Further, optimization of the kind of substrates used and reaction conditions permits the N—C bond to be formed by reacting palladium having a valency of 0 (zero), a phosphine ligand, and a base. Furthermore, the N—C bond may be formed in accordance with the method of Tetrahedron, 51(2), 353, 1995. The reaction may be carried out according to the method described, for example, in Intermediates 26, 27, 29, and 39 in WO 99/52872.

An organic base, such as diisopropylethylamine, N-methylmorpholine, dimethylaminopyridine, or triethylamine, is preferably added as an acid scavenger from the viewpoint of improving the yield. The addition of 2 to 10 equivalents of diisopropylethylamine is preferred.

The compound represented by formula (II) wherein $R^4$ has been substituted may be prepared by conventional or reductive N-alkylation followed by the introduction of group A into the primary amino group in the compound represented by formula (VI) or by the introduction of group A into the primary amino group in the compound represented by formula (VI) followed by N-alkylation of the secondary amino group, if necessary. The reaction may be carried out according to the method described in Intermediate 30 in WO 99/52872.

The compound represented by formula (VI) may be produced by reacting a compound represented by formula (IX)

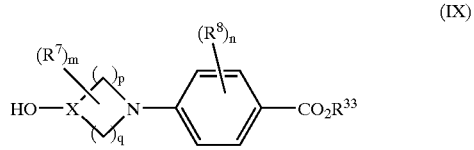

(IX)

wherein X, $R^7$, $R^8$, $R^{33}$, p, and q are as defined above, with phthalimide together with an azo compound in a reaction solvent such as tetrahydrofuran, benzene, toluene, dioxane, or dimethylformamide, preferably tetrahydrofuran, in the presence of a trialkylphosphine, preferably tributylphosphine, at −40 to 100° C., preferably −10 to 40° C., followed by the removal of the phthaloyl group. Azo compounds include 1,1'-(azodicarbonyl)dipiperidine, diethyl azodicarboxylate, and 1,1'-azobis(N,N-dimethylformamide). Among them, 1,1'-(azodicarbonyl) dipiperidine is preferred.

Alternatively, the compound represented by formula (VI) may be produced by converting the hydroxyl group in the compound represented by formula (IX) to a leaving group, for example, a sulfonyloxy group such as a methanesulfonyloxy group, or a halogen atom such as a bromine atom, allowing sodium azide or a combination of hydrazoic acid with an azo compound to act on the leaving group to convert the leaving group to an azide group, and then reducing the azide group. The reaction may be carried out according to the method described, for example, in Intermediates 35, 36, 41, 42, 43, 47, 48, 49, and 58 in WO 99/52872.

The compound represented by formula (II) in scheme 1, wherein D represents >$CR^5R^6$, may be produced, for example, by reacting 2-(chloromethyl)benzimidazole with ethyl 4-(piperazin-1-yl)benzoate in dimethyl sulfoxide in the presence of potassium carbonate at room temperature. This reaction may be carried out according to the method described in Examples 89 and 90 in WO 99/52872.

The compound represented by formula (II) in scheme 1, wherein D represents —O—, may be produced by reacting the hydroxyl group in the compound represented by formula (IX) with a basic atomic group having an alkylsulfonyl group, that is, a compound corresponding to group A. This reaction may be carried out in accordance with the method described, for example, in Japanese Patent Laid-Open No. 97818/1993 and EP 468766A1.

The compound represented by formula (II) in scheme 1, wherein D represents —S—, may be produced by halogenating the hydroxyl group in the compound represented by formula (IX) and reacting the halogen atom with a basic atomic group having group —SH, that is, a compound corresponding to group A. The reaction of the halogen atom with group —SH may be carried out in accordance with the method described, for example, in Res. Lab., Kohjin Co., Ltd., Japan Chem. Pharm. Bull. (1977), 25(10), 2624–37.

The compound represented by formula (II) in scheme 1, wherein D represents a bond, may be produced by introducing group A into a free secondary amine in a compound represented by formula (IX')

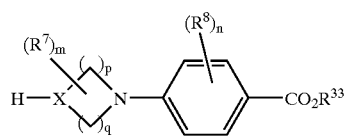

(IX')

wherein X, $R^7$, $R^8$, $R^{33}$, p, and q are as defined above.

The compound represented by formula (IX) and the compound represented by formula (IX') may be produced according to the method described, for example, in WO 99/52872 and WO 99/38849.

The compounds according to the present invention may also be synthesized according to scheme 2. In this scheme, A, D, X, J, $R^7$, $R^8$, $R^9$, $R^{10}$, $R^{11}$, m, n, p, and q are as defined above.

Scheme 2

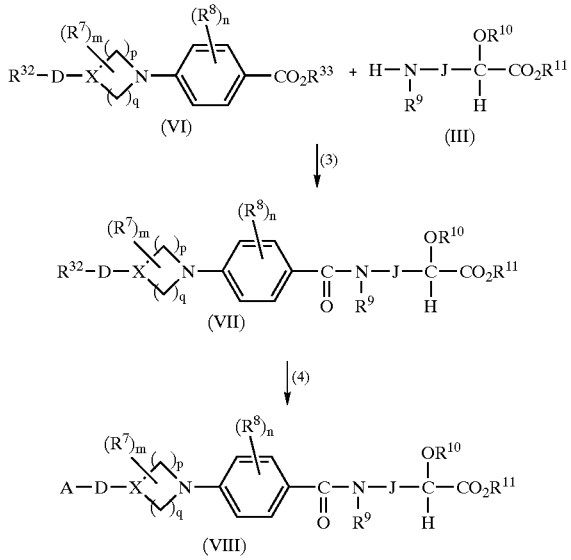

A compound represented by formula (VII) may be produced by hydrolyzing a benzoic ester represented by formula (VI), wherein $R^{33}$ represents $C_{1-6}$ alkyl or aralkyl, to give a compound represented by formula (VI), wherein $R^{33}$ represents a hydrogen atom and then reacting this compound with a compound represented by formula (III) to form an amide bond. More specifically, the compound represented by formula (VII) may be prepared by hydrolyzing the free carboxyl group in the compound represented by formula (VI), wherein $R^{33}$ represents a hydrogen atom with an alkali according to a conventional method and then reacting the compound thus obtained with the amine represented by formula (III) to perform condensation (step 3). In the compound represented by formula (VII), $R^{32}$ represents a protective group of amino. Protective groups of amino include Fmoc (9-fluorenylmethoxycarbonyl), t-butyloxycarbonyl, benzyloxycarbonyl, and p-methoxybenzyloxycarbonyl. Preferred is t-butyloxycarbonyl.

Next, the compound represented by formula (V) can be prepared by removing the protective group in the piperidine derivative portion, introducing a basic atomic group corresponding to group A, for example, pyrimidine, benzimidazole, or amidino, into the deprotected primary amine, and then, if necessary, converting the carboxylic ester portion to a free carboxyl group (step 4). The reaction may be carried out according to Intermediates 20, 21, and 22 and Examples 21 and 22 in WO 99/52872.

If necessary, the carboxylic ester portion (—COOR$^{11}$) in the compound represented by formula (VIII) may be converted to a free carboxyl group to produce the compound represented by formula (V).

The compound represented by formula (I), wherein X represents N and Z represents CH, may be produced from 4-bromobenzyl alcohol with the hydroxyl group being protected by the method described in WO 94/12181. Specifically, a phenylpiperidine derivative corresponding to formula (IX) can be produced by reacting lithiumized 4-bromobenzyl alcohol (with the hydroxyl group being protected) with N-Boc-4-piperidone to give a phenylpiperidine derivative, reductively removing the formed hydroxyl group, deprotecting the protected hydroxyl group, esterifying the deprotected hydroxyl group, and removing the Boc group. The compound represented by formula (I), wherein X represents N and Z represents CH, may be produced from the phenylpiperidine derivative according to scheme 1.

According to the production process of the present invention, the compounds according to the present invention can be efficiently synthesized by building block synthesis. Specifically, the starting material for the production of intermediates 1, 2, 3, 4, and 5 is L-isoserine or AHBA which is a starting material for commercially available semisynthetic aminoglycoside antibiotics, for example, isepamycin or arbekacin, and, thus, the efficient production process and purification process have already been established. Therefore, the production process according to the present invention advantageously comprises reliable steps.

Further, the production process according to the present invention is also advantageous in that the synthesis route is widely used. Since a hydroxyl group or a protected or modified hydroxyl group is located at the α-position on the C-terminal side of the compound according to the present invention, the compound according to the present invention is different from low-molecular integrin $\alpha_v\beta_3$ antagonist having sulfonamide at their α-position which has been reported, in reactivity. Specifically, in the building block on the C-terminal side which is located downstream of the synthesis route (in the present invention, for example, after the L-isoserine derivative has been bonded to the compound represented by formula (VI)), various reactions may be carried out under severe conditions, for example, after the deprotection of $R^{31}$ in the compound represented by formula (VII) in the scheme. This is because a highly reactive functional group, such as a sulfonamide group, is absent in the molecule. Specifically, regarding the compound after the removal of $R^{31}$ from the compound represented by formula (VII), the amino group preferentially reacts in a usual reaction, and, thus, excellent selectivity in chemical conversion to the compound represented by formula (V), as well as various chemical conversions can be expected. For this reason, the synthesis of integrin $\alpha_v\beta_3$ antagonist using the amine represented by formula (III) can be applied to the production of the compounds according to the present invention and, in addition, to the production of all of integrin $\alpha_v\beta_3$ antagonists using the amine represented by formula (III).

In the synthesis of the compound according to the present invention, for example, in scheme 1, an amino bond was first formed and the optionally substituted pyrimidine ring in the compound represented by the formula (V) was then reduced. Alternatively, in the compound represented by formula (II), the basic atomic group bonded to the primary amino group in the piperidine derivative, for example, the optionally substituted pyrimidine ring, may be reduced followed by the reaction for the formation of the amide bond.

In the compounds represented by formulae (IV) and (V) in the scheme, the atomic group, which has already been constructed in the molecule, for example, $R^7$, $R^8$, $R^9$, and $R^{10}$, may be if necessary further converted.

Use of Compounds/pharmaceutical Composition

The compounds according to the present invention have potent integrin $\alpha_v\beta_3$ antagonistic activity, as demonstrated in Pharmacological Test Example 1. Accordingly, the compounds according to the present invention can be used in the treatment of integrin $\alpha_v\beta_3$-mediated diseases. The integrin $\alpha_v\beta_3$ mediates cardiovascular diseases such as acute myocardial infarction, neointima formation hypertrophy, restenosis after PTCA/stent operation, unstable angina, arteria coronary syndrome, angina pectoris after PTCA/stent operation, arterial sclerosis, particularly atherosclerosis; angiogenesis-related diseases such as diabetic retinopathy, diabetic vascular complication, or vascular grafting; cerebrovascular diseases such as cerebral infarction; cancers such as solid tumors or metastasis thereof, immunological diseases such as arthritis, particularly rheumatic arthritis; and osteopathy such as osteoporosis, hypercalcemia, periodontitis, hyperparathyroidism, periarticular sore, or Paget's diseases (DN & P, 10 (8), 456 (1997)).

Further, as described in Pharmacological Test Example 2, the compounds according to the present invention have GP IIb/IIIa antagonistic activity and human platelet aggregation inhibitory activity. Therefore, the compounds according to the present invention can be used in the treatment of diseases where GP IIb/IIIa antagonism and the inhibition of human platelet aggregation are therapeutically effective. More specifically, the compounds according to the present invention can be used in the treatment of platelet thrombosis and thromboembolism during and after the treatment of thrombolysis and after angioplasty of coronary artery and other arteries and after bypassing of coronary artery, the improvement of peripheral circulating blood stream, and the inhibition of blood clotting during extracorporeal circulation. Furthermore, the compounds according to the present invention can be used in the treatment of thrombotic thrombocytopenic purpura and hemolytic uremic syndrome (Gendai Iryo, 29, (11), 2753 (1997)).

The compounds according to the present invention have potent integrin $\alpha_v\beta_3$ antagonistic activity and, at the same time, are highly soluble in water. Therefore, the compounds according to the present invention are advantageously suitable for intraveneous injection in the acute phase, intravenous drip infusion in the acute phase, and eye drop administration.

Further, the compounds according to the present invention have advantageously substantially no side effect, that is, have substantially no pharmacological activity which is not involved in integrin $\alpha_v\beta_3$ directly.

The compounds according to the present invention and pharmacologically acceptable salts and solvates thereof can be administered orally or parenterally by administration routes, for example, inhalation administration, rhinenchysis, instillation, subcutaneous administration, intravenous injection, intravenous drip infusion, intramuscular injection, rectal administration, or percutaneous administration, and thus may be formed into appropriate various dosage forms depending on oral or parenteral administration routes and administered to human and non-human animals.

The compounds according to the present invention may be formulated into, for example, oral preparation, such as tablets, capsules, chewable preparations, granules, powders, pills, particulates, troches, syrups, emulsions, suspensions, or solutions; liquids for external use such as inhalants, nasal drops, or eye drops; patches; injections such as intravenous injections, intramuscular injections, or intravenous drip infusions; preparations for rectal administrations; oleaginous suppositories; water-soluble suppositories; and liniments such as ointments depending upon applications thereof. Further, liquid preparations, such as injections or drops, may be provided, for example, as a lyophilized powdery pharmaceutical composition, which may be dissolved or suspended in water or other suitable vehicle, for example, physiological saline, glucose infusion, or buffer solution, before use.

These various preparations may be prepared by conventional methods with commonly used components, for example, excipients, extenders, binders, humidifiers, disintegrants, surface active agents, lubricants, dispersants, buffers, preservatives, dissolution aids, antiseptics, flavoring agents, analgesic agents, stabilizers and the like. Non-toxic additives usable herein include, for example, lactose, fructose, glucose, starch, gelatin, magnesium carbonate, synthetic magnesium silicate, talc, magnesium stearate, methylcellulose, carboxymethylcellulose or a salt thereof, gum arabic, olive oil, propylene glycol, polyethylene glycol, syrup, petrolatum, glycerin, ethanol, citric acid, sodium chloride, sodium sulfite, sodium phosphate, ascorbic acid, and cyclodextrins.

The dose of the compound according to the present invention in the medicament may vary depending on the dosage form. The dose is, however, generally 1.0 to 100% by weight, preferably 1.0 to 60% by weight, based on the whole composition.

Regarding the pharmaceuticals according to the present invention, the dose and the number of times of administration are not particularly limited, and may be appropriately determined depending on, for example, the purpose of treatment or prevention, the type of diseases, the age, weight, and severity of condition of patients. The dose for the treatment and prevention of coronary diseases and the like may be appropriately determined depending on, for example, the dosage route and the age, sex and severity of condition of patients, and the active ingredient may be administered usually in an amount of about 0.1 to 2,000 mg, preferably about 5 to 400 mg per day per adult. This dose may be administered at a time daily, divided doses of several times daily, or at a time every several days.

EXAMPLES

The present invention will be described with reference to the following examples, though it is not limited to these examples only.

Intermediate 1: t-Butyl 3-amino-(2S)-hydroxypropionate
Intermediate 2: t-Butyl 3-amino-(2S)-t-butoxypropionate The following reaction was carried out in a Fischer-Porter tube. Dimethoxyethane (76 ml) and 3.2 ml of concentrated sulfuric acid were added in that order to 4.0 g of 3-amino-(2S)-hydroxypropionic acid (L-isoserine), and the mixture was then cooled to −78° C. Isobutylene (38 ml) was added thereto, and the tube was sealed, followed by shaking at room temperature for 48 hr. The tube was then slowly opened, and isobutylene was removed by distillation at room temperature. The reaction mixture was then added dropwise to 128 ml of ice water, and the mixture was washed twice with 250 ml of ether, was cooled to 0° C., and was then neutralized with a 6 N aqueous sodium hydroxide solution. Further, solid sodium chloride was added to prepare a saturated solution, and the mixture was extracted four times with 100 ml of chloroform. The chloroform layers were combined, and the combined chloroform layers were dried over anhydrous sodium sulfate and were then concentrated under the reduced pressure to give 640 mg of a yellow oil. The yellow oil was purified by column chromatography on silica gel (64 g, chloroform-methanol-concentrated aqueous ammonia=20:1:0.05→10:1:0.1) to give 191 mg of intermediate 1 and 430 mg of intermediate 2.

Physicochemical properties of intermediate 1
(1) Color and form: Colorless columnar crystal
(2) Molecular formula: $C_7H_{15}NO_3$
(3) m.p.: 62–64° C.
(4) Mass spectrum (FABMS): m/z 162 (M+H)$^+$
(5) Specific rotation: $[\alpha]_D^{25}$ −8° (c 1.0, CHCl$_3$)
(6) $^1$H NMR spectrum (400 MHz, CDCl$_3$) δ (ppm); 1.50 (9H, s, t-Bu), 2.91 (1H, dd, CH$_2$NH$_2$), 3.02 (1H, dd, CH$_2$NH$_2$), 4.05 (1H, dd, COCH)

Physicochemical properties of intermediate 2
(1) Color and form: Colorless oil
(2) Molecular formula: $C_{11}H_{23}NO_3$
(3) Mass spectrum (FABMS): m/z 218 (M+H)$^+$
(4) Specific rotation: $[\alpha]_D^{25}$ −47° (c 1.0, CH$_2$Cl$_2$)
(5) $^1$H NMR spectrum (400 MHz, CDCl$_3$) δ (ppm): 1.22 (9H, s, t-Bu), 1.47 (9H, s, CO$_2$-t-Bu), 2.82 (1H, dd, CH$_2$NH$_2$), 2.89 (1H, dd, CH$_2$NH$_2$), 3.85 (1H, dd, COCH)

Example 1 t-Butyl(2S)-hydroxy-3-[4-{4-(pyrimidin-2-yl)piperazin-1-yl}benzoylamino]propionate Dimethylformamide (5.0 ml) was added to 32.1 mg of 4-{4-(pyrimidin-2-yl)piperazin-1-yl}benzoic acid (WO 99/38849) to prepare a solution, and 24.0 mg of 1-hydroxybenzotriazole and 0.060 ml of N-methylmorpholine were successively added to the solution. A solution of 17.9 mg of intermediate 1 in 5.0 ml of dimethylformamide and 45.6 mg of 1-ethyl-3-(3-dimethylaminopropyl)carbodiimide hydrochloride were added in that order to the mixture, and a reaction was allowed to proceed at room temperature for 24 hr. A saturated aqueous sodium hydrogencarbonate solution (100 ml) was added to the reaction solution. The mixture was extracted three times with 100 ml of ethyl acetate, and the ethyl acetate layers were combined. The combined ethyl acetate layers were washed with 100 ml of water, were dried over anhydrous magnesium sulfate, and were then filtered. The filtrated was concentrated under the reduced pressure. The residue was purified by column chromatography on silica gel (57 g, ethyl acetate-methanol=15:1) to give 37.6 mg of the title compound.

Physicochemical properties of compound prepared in Example 1
(1) Color and form: Colorless solid
(2) Molecular formula: $C_{12}H_{29}N_5O_4$
(3) Mass spectrum (TSP (thermospray) MS): m/z 428 (M+H)$^+$
(4) Specific rotation: $[\alpha]_D^{25}$ +8° (c 1.0, MeOH)
(5) $^1$H NMR spectrum (400 MHz, CDCl$_3$) δ (ppm): 1.47 (9H, s, t-Bu), 3.38 (4H, app (apparent) br t, piperazine), 3.76 (1H, ddd, CONHCH$_2$), 3.83 (1H, ddd, CONHCH$_2$), 3.99 (4H, app br t, piperazine), 4.26 (1H, m, CONHCH$_2$CH), 6.54 (1H, t, pyrimidine), 6.92 (2H, d, C$_6$H$_4$), 7.69 (2H, d, C$_6$H$_4$), 8.34 (2H, d, pyrimidine)

Example 2

(2S)-Hydroxy-3-[4-{4-(pyrimidin-2-yl)piperazin-1-yl}benzoylamino]propionic acid

Methylene chloride (3.0 ml) and 3.0 ml of trifluoroacetic acid were successively added to 37.6 mg of the compound prepared in Example 1 to prepare a solution, and a reaction was allowed to proceed at room temperature for 3 hr. The reaction solution was concentrated under the reduced pressure. The residue was dissolved in 2.0 ml of methanol, and the solution was added dropwise to 200 ml of isopropyl ether at 0° C. The precipitated insolubles were collected by filtration and were dried to give 15.2 mg of ditrifluoroacetate of the title compound.

Physicochemical properties of compound prepared in Example 2
(1) Color and form: Colorless solid (as ditrifluoroacetate)
(2) Molecular formula: $C_{18}H_{21}N_5O_4$
(3) Mass spectrum (TSPMS): m/z 372 (M+H)$^+$
(4) Specific rotation: $[\alpha]_D^{25}$ −3° (c 0.3, MeOH) (as ditrifluoroacetate)
(5) $^1$H NMR spectrum (400 MHz, CD$_3$OD) (as ditrifluoroacetate) δ (ppm): 3.38 (4H, app br t, piperazine), 3.60 (1H, dd, CONHCH$_2$), 3.76 (1H, dd, CONHCH$_2$), 3.95 (4H, app br t, piperazine), 4.35 (1H, dd, CONHCH$_2$CH), 6.61 (1H, t, pyrimidine), 7.02 (2H, d, C$_6$H$_4$), 7.76 (2H, d, C$_6$H$_4$), 8.34 (2H, d, pyrimidine)

Example 3 t-Butyl(2S)-hydroxy-3-[4-{4-(pyrimidin-2-ylamino) piperidin-1-yl}benzoylamino]propionate Dimethylformamide (3.2 ml) was added to 63.8 mg of 4-{4-(pyrimidin-2-ylamino)piperidin-1-yl}benzoic acid (WO 99/52872), and 142 mg of benzoytriazol-1-yloxytri (dimethylamino)phosphonium hexafluorophosphate was added thereto. Diisopropylethylamine (0.056 ml) and 3.2 ml of methylene chloride were added to the mixture, followed by stirring at room temperature for 2 hr to prepare a transparent reaction solution. Separately, 3.2 ml of methylene chloride was added to 23.0 mg of intermediate 1 to prepare a solution, 0.028 ml of diisopropylethylamine was added to the solution, and the mixture was cooled to 0° C. The reaction solution prepared above was added dropwise to this solution at 0° C., and a reaction was allowed to proceed at room temperature for 16 hr. The reaction solution was concentrated under the reduced pressure. The residue was extracted with 20 ml of ethyl acetate, and the extract was washed with a saturated aqueous sodium hydrogencarbonate solution and saturated brine in that order and was then dried over anhydrous sodium sulfate. The ethyl acetate layer was concentrated under the reduced pressure, and the residue was purified by preparative thin-layer chromatography (development system: chloroform-methanol-concentrated aqueous ammonia=10:1:0.1) to give 32.1 mg of the title compound.

Physicochemical properties of compound prepared in Example 3
(1) Color and form: Colorless syrup
(2) Molecular formula: $C_{23}H_{31}N_5O_4$
(3) Mass spectrum (TSPMS): m/z 442 (M+H)$^+$
(4) Specific rotation: $[\alpha]_D^{25}$ −12° (c 0.9, CHCl$_3$)
(5) $^1$H NMR spectrum (400 MHz, CDCl$_3$) δ (ppm): 1.47 (9H, s, t-Bu), 1.61 (2H, m, piperidine), 2.17 (2H, br d, piperidine), 3.04 (2H, br t, piperidine), 3.75–3.86 (4H, m, piperidine, CONHCH$_2$), 4.04 (1H, m, piperidine), 4.26 (1H, dd, CONHCH$_2$CH), 6.54 (1H, t, pyrimidine), 6.89 (2H, d, C$_6$H$_4$), 7.66 (2H, d, C$_6$H$_4$), 8.28 (2H, d, pyrimidine)

Example 4 t-Butyl (2S)-t-butoxy-3-[4-{4-(pyrimidin-2-ylamino) piperidin-1-yl}benzoylamino]propionate Dimethylformamide (5.3 ml) and 5.3 ml of methylene chloride were added to 128 mg of 4-{4-(pyrimidin-2-ylamino)piperidin-1-yl}benzoic acid and 285 mg of benzotriazol-1-yloxytri(dimethylamino)phosphonium hexafluorophosphate to prepare a solution. Diisopropylethylamine (0.11 ml) was added to the solution, and a reaction was allowed to proceed at room temperature for 2 hr. Separately, 5.3 ml of methylene chloride was added to 85.0 mg of intermediate 2 to prepare a solution, 0.056 ml of diisopropylethylamine was added to the solution, and the mixed solution was cooled to 0° C. The above reaction solution was added dropwise to this mixed solution at 0° C., and a reaction was allowed to proceed at room temperature for 3 hr. The reaction solution was concentrated under the reduced pressure. The residue was extracted with 60 ml of ethyl acetate. The extract was washed with a saturated aqueous sodium hydrogencarbonate solution and saturated brine in that order and was then dried over anhydrous sodium sulfate. The ethyl acetate layer was concentrated under the reduced pressure, and the residue was purified by column chromatography on silica gel (20 g, chloroform-methanol=30:1) to give 174 mg of the title compound.

Physicochemical properties of compound prepared in Example 4
(1) Color and form: Colorless syrup
(2) Molecular formula: $C_{27}H_{39}N_5O_4$
(3) Mass spectrum (TSPMS): m/z 498 (M+H)$^+$
(4) Specific rotation: $[\alpha]_D^{25}$ −4° (c 1.0, CHCl$_3$)
(5) $^1$H NMR spectrum (400 MHz, CDCl$_3$) δ (ppm): 1.21 (9H, s, t-Bu), 1.46 (9H, S, CO$_2$-t-Bu), 1.61 (2H, m, piperidine), 2.17 (2H, br d, piperidine), 3.04 (2H, br t, piperidine), 3.47 (1H, ddd, CONHCH$_2$), 3.80 (2H, br d, piperidine), 3.81 (1H, ddd, CONHCH$_2$), 4.05 (1H, m, piperidine), 4.15 (1H, dd, CONHCH$_2$CH), 6.54 (1H, t, pyrimidine), 6.91 (2H, d, C$_6$H$_4$), 7.67 (2H, d, C$_6$H$_4$), 8.28 (2H, d, pyrimidine)

Example 5

(2S)-Hydroxy-3-[4-{4-(pyrimidin-2-ylamino) piperidin-1-yl}benzoylamino]propionic acid Methylene chloride (4.0 ml) and 0.20 ml of anisole were added to 164 mg of the compound prepared in Example 4, and the mixture was cooled to 0° C. Trifluoroacetic acid (4.0 ml) was added thereto at 0° C., and a reaction was allowed to proceed at room temperature for 2 hr. The reaction solution was concentrated under the reduced pressure, and the residue was subjected to azeotropic distillation twice each with 4.0 ml of toluene. The product obtained by the azeotropic distillation was first purified by column chromatography on silica gel (16 g, chloroform-methanol-concentrated aqueous ammonia=9:2:0.1) and was then purified by Sephadex LH-20 (270 ml, methanol-concentrated aqueous ammonia=9:1) to give 144 mg of the title compound.

Physicochemical properties of compound prepared in Example 5
(1) Color and form: Colorless solid
(2) Molecular formula: C$_{19}$H$_{23}$N$_5$O$_4$
(3) Mass spectrum (TSPMS): m/z 386 (M+H)$^+$
(4) Specific rotation: [α]$_D^{25}$ −12° (c 0.2, 10% c. NH$_4$OH/ MeOH)
(5) $^1$H NMR spectrum (400 MHz, DMSO-d$_6$) δ (ppm): 1.54 (2H, br q, piperidine), 1.92 (2H, br d, piperidine), 2.90 (2H, br t, piperidine), 3.86 (2H, br d, piperidine), 3.93 (1H, m, piperidine), 6.55 (1H, t, pyrimidine), 6.96 (2H, d, C$_6$H$_4$), 7.69 (2H, d, C$_6$H$_4$), 8.27 (2H, d, pyrimidine)

The compound of Example 5 could also be produced by reacting the compound prepared in Example 3 under the same conditions as described above.

Example 6

(2S)-Hydroxy-3-[4-{4-(1,4,5,6-tetrahydropyrimidin-2-ylamino)piperidin-1-yl}benzoylamino]-propionic acid 1,4-Dioxane (7.0 ml), 2.0 ml of water, and 1.0 ml of 1 N hydrochloric acid were added in that order to 76.8 mg of the compound prepared in Example 5 to prepare a solution. To the solution was added 24 mg of 10% palladium-carbon. A reaction was allowed to proceed in a hydrogen atmosphere at room temperature for 16 hr. The insolubles were filtered and were then washed twice with 2.0 ml of a solvent having the same composition as the mixed solvent used in the reaction, and the filtrate and the washings were combined followed by concentration under the reduced pressure. The residue was purified by Sephadex LH-20 (40 ml, 1,4-dioxane-water=7:3) to give 47.5 mg of dihydrochloride of the title compound.

Physicochemical properties of compound prepared in Example 6
(1) Color and form: Colorless solid (as dihydrochloride)
(2) Molecular formula: C$_{19}$H$_{27}$N$_5$O$_4$
(3) Mass spectrum (FABMS): m/z 390 (M+H)$^+$
(4) Specific rotation: [α]$_D^{25}$ −3° (c 1.2, H$_2$O) (dihydrochloride)
(5) $^1$H NMR spectrum (400 MHz, D$_2$O) (dihydrochloride) δ (ppm): 1.65 (2H, m, piperidine), 1.77 (2H, quintet, tetrahydropyrimidine), 2.03 (2H, br d, piperidine), 3.17 (4H, t, tetrahydropyrimidine), 3.18 (2H, br t, piperidine), 3.51 (1H, m, piperidine), 3.57 (2H, dd, CONHCH$_2$), 3.61 (2H, br d, piperidine), 4.26 (1H, t, CONHCH$_2$CH), 7.25 (2H, d, C$_6$H$_4$), 7.66 (2H, d, C$_6$H$_4$)

Example 7

(2S)-Acetoxy-3-[4-{4-(1,4,5,6-tetrahydropyrimidin-2-ylamino)piperidin-1-yl}benzoylamino]-propionic acid Methylene chloride (0.50 ml) and 0.025 ml of anisole were added to 28.6 mg of the compound prepared in Example 3 to prepare a solution which was then cooled to 0° C. Trifluoroacetic acid (0.50 ml) was added to the cooled solution, and a reaction was allowed to proceed at room temperature for 5 hr. The reaction solution was concentrated under the reduced pressure. The residue was subjected to azeotropic distillation twice with 2.0 ml of toluene. Subsequently, the product obtained by the azeotropic distillation was washed twice with 4.0 ml of isopropyl ether and was then dried to prepare 44.2 mg of trifluoroacetate of the compound of Example 5 in an unpurified form. Acetic acid (2.5 ml) and 0.23 ml of concentrated hydrochloric acid were added in that order to a 38.6 mg portion of the compound thus obtained to prepare a solution. To the solution was added 23 mg of 10% palladium-carbon. The mixture was subjected to catalytic reduction under a hydrogen pressure of 3 atm at room temperature for 2.5 hr with shaking. The insolubles were filtered and were washed twice with acetic acid. The filtrate and the washings were combined, followed by concentration under the reduced pressure. The residue was subjected to azeotropic distillation twice with toluene, and the product obtained by the azeotropic distillation was first purified by preparative thin-layer chromatography (development system: methylene chloride-ethanol-water-concentrated aqueous ammonia=8:8:1:1) and was then purified by Sephadex LH-20 (methanol, 30 ml) to give 3.0 mg of the title compound. At that time, a minor amount of the compound of Example 6 was isolated.

Physicochemical properties of compound prepared in Example 7
(1) Color and form: Colorless solid
(2) Molecular formula: C$_{21}$H$_{29}$N$_5$O
(3) Mass spectrum (TSPMS): m/z 432 (M+H)$^+$
(4) Specific rotation: [α]$_D^{25}$ −23° (c 0.1, MeOH)
(5) $^1$H NMR spectrum (400 MHz, CD$_3$OD) δ (ppm): 1.57 (2H, br q, piperidine), 1.95 (2H, quintet, tetrahydropyrimidine), 1.96 (2H, br d, piperidine), 2.09 (3H, s, Ac), 2.90 (2H, br t, piperidine), 3.36 (4H, t, tetrahydropyrimidine), 3.49 (1H, m, piperidine), 3.74 (1H, dd, CONHCH$_2$), 3.78 (2H, br d, piperidine), 3.80 (1H, dd, CONHCH$_2$), 5.06 (1H, dd, CONHCH$_2$CH), 6.92 (2H, d, C$_6$H$_4$), 7.69 (2H, d, C$_6$H$_4$)

Intermediate 3: t-Butyl 4-amino-(2S)-hydroxybutyrate
Intermediate 4: t-Butyl 4-amino-(2S)-t-butoxybutyrate The following reaction was carried out in a Fischer-Porter tube. Dimethoxyethane (76 ml) and 3.2 ml of concentrated sulfuric acid were added in that order to 4.0 g of 4-amino-(2S)-hydroxybutyric acid (AHBA), and the mixture was then cooled to −78° C. Isobutylene (38 ml) was added thereto, and the tube was sealed, followed by stirring at room temperature for 96 hr. The tube was then slowly opened, and isobutylene was removed by distillation at room temperature. The reaction mixture was then added dropwise to 128 ml of ice water, and the mixture was washed twice with 250 ml of ether, was cooled to 0° C., and was then neutralized with a 6 N aqueous sodium hydroxide solution. Further, solid sodium chloride was added to prepare a saturated solution, and the mixture was extracted four times with 100 ml of chloroform. The chloroform layers were combined, and the combined chloroform layers were dried over anhydrous sodium sulfate and were then concentrated under the reduced pressure to give 250 mg of a yellow oil. The yellow oil was purified by column chromatography on silica gel (30 g, chloroform-methanol-concentrated aqueous ammonia= 20:1:0.05→9:2:0.1) to give 37.9 mg of intermediate 3 and 161 mg of intermediate 4.

Physicochemical properties of intermediate 3
(1) Color and form: Colorless oil
(2) Molecular formula: $C_8H_{17}NO_3$
(3) Mass spectrum (TSPMS): m/z 176 (M+H)$^+$
(4) Specific rotation: $[\alpha]_D^{25}$ −30° (c 1.0, $CHCl_3$)
(5) $^1$H NMR spectrum (400 MHz, $CDCl_3$) δ (ppm): 1.49 (9H, s, t-Bu), 1.77 (1H, m, $CH_2CH_2NH_2$), 1.93 (1H, m, $CH_2CH_2NH_2$), 2.93 (1H, dd, $CH_2NH_2$), 2.95 (1H, dd, $CH_2NH_2$), 4.22 (1H, dd, COCH)

Physicochemical properties of intermediate 4
(1) Color and form: Colorless oil
(2) Molecular formula: $C_{12}H_{25}NO_3$
(3) Mass spectrum (TSPMS): m/z 232 (M+H)$^+$
(4) Specific rotation: $[\alpha]_D^{25}$ −41° (c 1.0, $CH_2Cl_2$)
(5) $^1$H NMR spectrum (400 MHz, $CDCl_3$) δ (ppm): 1.20 (9H, s, t-Bu), 1.46 (9H, s, $CO_2$-t-Bu), 1.75 (2H, q, $CH_2CH_2NH_2$), 2.76 (1H, ddd, $CH_2NH_2$), 2.83 (1H, ddd, $CH_2NH_2$), 3.95 (1H, dd, COCH)

Example 8 t-Butyl(2s)-t-butoxy-4-[4-{4-(pyrimidin-2-ylamino) piperidin-1-yl}benzoylamino]butyrate Dimethylformamide (5.3 ml) and 5.3 ml of methylene chloride were added to 128 mg of 4-{4-(pyrimidin-2-ylamino)piperidin-1-yl}benzoic acid and 285 mg of benzotriazol-1-yloxytri(dimethylamino)phosphonium hexafluorophosphate to prepare a solution. Diisopropylethylamine (0.11 ml) was added to the solution, and a reaction was allowed to proceed at room temperature for 2 hr. Separately, 5.3 ml of methylene chloride was added to 90.5 mg of intermediate 4 to prepare a solution. Diisopropylethylamine (0.056 ml) was added to the solution, and the mixture was cooled to 0° C. The reaction solution prepared above was added dropwise at 0° C. to this solution, and a reaction was allowed to proceed at room temperature for 3 hr. The reaction solution was concentrated under the reduced pressure. The residue was extracted with 60 ml of ethyl acetate, followed by washing with a saturated aqueous sodium hydrogencarbonate solution and saturated brine in that order. The extract was then dried over anhydrous sodium sulfate. The ethyl acetate layer was concentrated under the reduced pressure, and the residue was purified by column chromatography on silica gel (50 g, chloroform-methanol-concentrated aqueous ammonia=90:3:0.1) to give 200 mg of the title compound.

Physicochemical properties of compound prepared in Example 8
(1) Color and form: Colorless solid
(2) Molecular formula: $C_{28}H_{41}N_5O_4$
(3) Mass spectrum (TSPMS): m/z 512 (M+H)$^+$
(4) Specific rotation: $[\alpha]_D^{25}$ −13° (c 1.0, $CHCl_3$)
(5) $^1$H NMR spectrum (400 MHz, $CDCl_3$) δ (ppm): 1.23 (9H, s, t-Bu), 1.46 (9H, s, $CO_2$-t-Bu), 1.62 (2H, m, piperidine), 1.96 (2H, m, $CONHCH_2CH_2$), 2.17 (2H, br d, piperidine), 3.03 (2H, br t, piperidine), 3.51 (1H, dddd, $CONHCH_2$), 3.62 (1H, dddd, $CONHCH_2$), 3.79 (2H, br d, piperidine), 4.04 (1H, m, piperidine), 4.07 (1H, dd, $CONHCH_2CH_2CH$), 6.54 (1H, t, pyrimidine), 6.90 (2H, d, $C_6H_4$), 7.70 (2H, d, $C_6H_4$), 8.28 (2H, d, pyrimidine)

Example 9

(2S)-Hydroxy-4-[4-{4-(pyrimidin-2-ylamino) piperidin-1-yl}benzoylamino]butyric acid Methylene chloride (4.0 ml) and 0.20 ml of anisole were added to 190 mg of the compound prepared in Example 8, and the mixture was cooled to 0° C. Trifluoroacetic acid (4.0 ml) was added thereto at 0° C., and a reaction was allowed to proceed at room temperature for 6 hr. The reaction solution was concentrated under the reduced pressure. The residue was subjected to azeotropic distillation twice with 8.0 ml of toluene, and the product obtained by the azeotropic distillation was washed twice with 8.0 ml of isopropyl ether. The product was first purified by column chromatography on silica gel (20 g, chloroform-methanol-concentrated aqueous ammonia=9:3:0.3) and was then purified by Sephadex LH-20 (280 ml, methanol-concentrated aqueous ammonia= 9:1) to give 148 mg of the title compound.

Physicochemical properties of compound prepared in Example 9
(1) Color and form: Colorless solid
(2) Molecular formula: $C_{20}H_{25}N_5O_4$
(3) Mass spectrum (TSPMS): m/z 400 (M+H)$^+$
(4) Specific rotation: $[\alpha]_D^{25}$ −5° (c 1.0, MeOH)
(5) $^1$H NMR spectrum (400 MHz, $CD_3OD$) δ (ppm): 1.64 (2H, br q, piperidine), 1.86 (1H, m, $CONHCH_2CH_2$), 2.08 (3H, m, piperidine, $CONHCH_2CH_2$), 2.98 (2H, br t, piperidine), 3.51 (2H, m, $CONHCH_2$), 3.88 (2H, br d, piperidine), 3.97 (1H, m, piperidine), 4.03 (1H, br dd, $CONHCH_2CH_2CH$), 6.59 (1H, t, pyrimidine), 6.98 (2H, d, $C_6H_4$), 7.72 (2H, d, $C_6H_4$), 8.26 (2H, d, pyrimidine)

Example 10

(2S)-Hydroxy-4-[4-{4-(1,4,5,6-tetrahydropyrimidin-2-ylamino)piperidin-1-yl}benzoylamino]butyric acid 1,4-Dioxane (12 ml), 3.4 ml of water, and 1.7 ml of 1 N hydrochloric acid were added in that order to 132 mg of the compound prepared in Example 9 to prepare a solution. To the solution was added 43 mg of 10% palladium-carbon. A reaction was allowed to proceed in a hydrogen atmosphere at room temperature for 26 hr. The insolubles were filtered and were washed twice with 4.0 ml of a solvent having the same composition as the mixed solvent used in the reaction. The filtrate and the washings were combined, followed by concentration under the reduced pressure. The residue was first purified by Sephadex LH-20 (50 ml, 1,4-dioxane-water=7:3) to give 100 mg of the title compound as a crude compound. The crude compound was then purified by preparative thin-layer chromatography (development system: chloroform-ethanol-water-concentrated aqueous ammonia=8:8:1:1) and was finally purified by Sephadex LH-20 (60 ml, methanol-water-concentrated aqueous ammonia=8:1:1) to give 37.7 mg of the title compound.

Physicochemical properties of compound prepared in Example 10

(1) Color and form: Colorless solid
(2) Molecular formula: $C_{20}H_{29}N_5O_4$
(3) Mass spectrum (TSPMS): m/z 404 (M+H)$^+$
(4) Specific rotation: $[\alpha]_D^{25}$ −7° (c 1.0, MeOH-H$_2$O-c. NH$_4$OH=8:1:1)
(5) $^1$H NMR spectrum (400 MHz, CD$_3$OD-20% ND$_4$OD/D$_2$O=5:1) δ (ppm): 1.60 (2H, m, piperidine), 1.86 (1H, ddd, CONHCH$_2$CH$_2$), 1.96 (2H, quintet, tetrahydropyrimidine), 2.03 (2H, br d, piperidine), 2.07 (1H, m, CONHCH$_2$CH$_2$), 2.98 (2H, br t, piperidine), 3.38 (4H, t, tetrahydropyrimidine), 3.44–3.62 (3H, m, piperidine, CONHCH$_2$), 3.83 (2H, br d, piperidine), 4.00 (1H, dd, CONHCH$_2$CH$_2$CH), 7.00 (2H, d, C$_6$H$_4$), 7.73 (2H, d, C$_6$H$_4$)

Intermediate 5: Benzhydryl 3-amino-(2S)-hydroxypropionate

Methanol (50 ml) was added to 1.00 g of 3-amino-(2S)-hydroxypropionic acid (L-isoserine) and 1.81 g of p-toluenesulfonic acid monohydrate to prepare a solution. Diphenyldiazomethane (16.1 g) was added to the solution at room temperature over a period of one hr. The reaction solution was concentrated under the reduced pressure. The residue was extracted with 100 ml of chloroform, followed by washing with a saturated aqueous sodium hydrogencarbonate solution. The chloroform layer was dried over anhydrous sodium sulfate and was concentrated under the reduced pressure. The residue was purified by column chromatography on silica gel (100 g, chloroform-methanol=20:1) to give 1.25 g of intermediate 5.

Physicochemical properties of intermediate 5

(1) Color and form: Colorless needle-like crystal
(2) Molecular formula: $C_{16}H_{17}NO_3$
(3) m.p.: 65–66° C.
(4) Mass spectrum (TSPMS): m/z 272 (M+H)$^+$
(5) Specific rotation: $[\alpha]_D^{25}$ −20° (c 1.0, MeOH)
(6) $^1$H NMR spectrum (400 MHz, CDCl$_3$) δ (ppm): 3.04 (1H, dd, CH$_2$NH$_2$), 3.11 (1H, dd, CH$_2$NH$_2$), 4.28 (1H, dd, COCH), 6.96 (1H, s, CHPh$_2$), 7.30–7.38 (10H, m, Ph)

Example 11

Benzhydryl 3-[3-fluoro-4-{4-(pyrimidin-2-ylamino) piperidin-1-yl}benzoylamino]-(2S)-hydroxypropionate Dimethylformamide (2.1 ml) and 2.1 ml of methylene chloride were added to 50.0 mg of 3-fluoro-4-{4-(pyrimidin-2-ylamino)piperidin-1-yl}benzoic acid (WO 99/52872) and 55.0 mg of benzotriazol-1-yloxytri (dimethylamino)phosphonium hexafluorophosphate to prepare a solution. Diisopropylethylamine (0.041 ml) was added to the solution, and a reaction was allowed to proceed at room temperature for 2 hr. Separately, 2.1 ml of methylene chloride was added to 51.5 mg of intermediate 5 to prepare a solution. Diisopropylethylamine (0.020 ml) was added to the solution, and the mixture was cooled to 0° C. The reaction solution prepared above was added dropwise at 0° C. to the solution, and a reaction was allowed to proceed at room temperature for 48 hr. The reaction solution was concentrated under the reduced pressure. The residue was extracted with 30 ml of ethyl acetate, followed by washing with a saturated aqueous sodium hydrogencarbonate solution and saturated brine in that order. The extract was then dried over anhydrous sodium sulfate. The ethyl acetate layer was concentrated under the reduced pressure. The residue was purified by column chromatography on silica gel (30 g, chloroform-methanol-concentrated aqueous ammonia=30:1:0.05) to give 90.0 mg of the title compound.

Physicochemical properties of compound prepared in Example 11

(1) Color and form: Colorless solid
(2) Molecular formula: $C_{32}H_{32}N_5O_4F$
(3) Mass spectrum (TSPMS): m/z 570 (M+H)$^+$
(4) Specific rotation: $[\alpha]_D^{25}$ −24° (c 1.0, CHCl$_3$)
(5) $^1$H NMR spectrum (400 MHz, CDCl$_3$) δ (ppm): 1.71 (2H, m, piperidine), 2.18 (2H, br d, piperidine), 2.94 (2H, br t, piperidine), 3.53 (2H, br d, piperidine), 3.79 (1H, ddd, CONHCH$_2$), 3.97 (1H, ddd, CONHCH$_2$), 4.01 (1H, m, piperidine), 4.52 (1H, dd, CONHCH$_2$CH), 6.53 (1H, t, pyrimidine), 6.88 (1H, dd, C$_6$H$_3$), 6.92 (1H, s, CHPh$_2$), 7.23–7.35 (12H, m, CHPh$_2$, C$_6$H$_3$), 8.28 (2H, d, pyrimidine)

Example 12 t-Butyl (2S)-t-butoxy-3-[3-fluoro-4-{4-pyrimidin-2-ylamino)piperidin-1-yl}benzoylamino]-propionate Dimethylformamide (4.2 ml) and 4.2 ml of methylene chloride were added to 100 mg of 3-fluoro-4-{4-(pyrimidin-2-ylamino)piperidin-1-yl}benzoic acid and 210 mg of benzotriazol-1-yloxytri(dimethylamino)phosphonium hexafluorophosphate. Diisopropylethylamine (0.083 ml) was added thereto, and a reaction was allowed to proceed at room temperature for 2 hr to prepare a transparent solution. Separately, 4.2 ml of methylene chloride was added to 68.7 mg of intermediate 2 to prepare a solution. Diisopropylethylamine (0.041 ml) was added to the solution, and the mixture was cooled to 0° C. The reaction solution prepared above was added dropwise at 0° C. to this solution, and a reaction was allowed to proceed at room temperature for 16 hr. The reaction solution was concentrated under the reduced pressure. The residue was extracted with 60 ml of ethyl acetate, followed by washing with a saturated aqueous sodium hydrogencarbonate solution and saturated brine in that order. The extract was then dried over anhydrous sodium sulfate. The ethyl acetate layer was concentrated under the reduced pressure. The residue was purified by column chromatography on silica gel (40 g, chloroform-methanol-concentrated aqueous ammonia=30:1:0.03) to give 135 mg of the title compound.

Physicochemical properties of compound prepared in Example 12

(1) Color and form: Colorless solid
(2) Molecular formula: $C_{27}H_{38}N_5O_4F$
(3) Mass spectrum (TSPMS): m/z 516 (M+H)$^+$
(4) Specific rotation: $[\alpha]_D^{25}$ −6° (c 1.0, CHCl$_3$)
(5) $^1$H NMR spectrum (400 MHz, CDCl$_3$) δ (ppm): 1.22 (9H, s, t-Bu), 1.46 (9H, s, CO$_2$-t-Bu), 1.72 (2H, m, piperidine), 2.20 (2H, br d, piperidine), 2.95 (2H, br t, piperidine), 3.52 (1H, ddd, CONHCH$_2$), 3.55 (2H, br d, piperidine), 3.77 (1H, ddd, CONHCH$_2$), 4.02 (1H, m, piperidine), 4.14 (1H, dd, CONHCH$_2$CH), 6.54 (1H, t, pyrimidine), 6.95 (1H, dd, C$_6$H$_3$), 7.45 (1H, dd, C$_6$H$_3$), 7.47 (1H, dd, C$_6$H$_3$), 8.29 (2H, d, pyrimidine)

Example 13

3-[3-Fluoro-4-{4-(pyrimidin-2-ylamino)piperidin-1-yl}benzoylamino]-(2S)-hydroxypropionic acid Methylene chloride (3.0ml) and 0.15 ml of anisole were added to 124 mg of the compound prepared in Example 12, and the mixture was cooled to 0° C. Trifluoroacetic acid (3.0 ml) was added thereto at 0° C., and a reaction was allowed to proceed at room temperature for 5 hr. The reaction solution was concentrated under the reduced pressure. The residue was subjected to azeotropic distillation twice with 4.0 ml of toluene, and the product obtained by the azeotropic distillation was washed twice with 6.0 ml of isopropyl ether. The product was first purified by preparative thin-layer chromatography (development system: chloroform-methanol-concentrated aqueous ammonia=9:4:0.4) and was then purified by Sephadex LH-20 (190 ml, ethanol-water-concentrated aqueous ammonia=8:1:1) to give 87.0 mg of the title compound.

Physicochemical properties of compound prepared in Example 13

(1) Color and form: Colorless solid
(2) Molecular formula: $C_{19}H_{22}N_5O_4F$
(3) Mass spectrum (TSPMS): m/z 404 (M+H)$^+$
(4) Specific rotation: $[\alpha]_D^{25}$ −15° (c 0.7, MeOH-H$_2$O-c.NH$_4$OH=8:1:1)
(5) $^1$H NMR spectrum (400 MHz, DMSO-d$_6$) δ (ppm): 1.65 (2H, br q, piperidine), 1.96 (2H, br d, piperidine), 2.84 (2H, br t, piperidine), 3.48 (2H, br d, piperidine), 3.80–3.94 (2H, m, piperidine, CONHCH$_2$CH), 6.55 (1H, t, pyrimidine), 7.08 (1H, dd, C$_6$H$_3$), 7.58 (1H, br dd, C$_6$H$_3$), 7.61 (1H, br d, C$_6$H$_3$), 8.27 (2H, d, pyrimidine)

The compound of Example 13 could also be produced by reacting the compound prepared in Example 11 under the same conditions as described above.

Example 14

3-[3-Fluoro-4-{4-(1,4,5,6-tetrahydropyrimidin-2-ylamino)piperidin-1-yl}benzoylamino]-(2S)-hydroxypropionic acid 1,4-Dioxane (8.4 ml), 2.4 ml of water, and 1.2 ml of 1 N hydrochloric acid were added in that order to 82.4 mg of the compound prepared in Example 13 to prepare a solution. To this solution was added 31 mg of 10% palladium-carbon. A reaction was then allowed to proceed in a hydrogen atmosphere at room temperature for 5 hr. The insolubles were filtered and were washed twice with 4.0 ml of a solvent having the same composition as the mixed solvent used in the reaction. The filtrate and the washings were combined, followed by concentration under the reduced pressure. The residue was purified by column chromatography on silica gel (12 g, ethanol-water-concentrated aqueous ammonia= 7:1:1) to give 25.9 mg of a solid. The solid was washed twice with 2.0 ml of water and was then heat dried over diphosphorus pentaoxide to give 19.9 mg of the title compound.

Physicochemical properties of compound prepared in Example 14

(1) Color and form: Colorless solid
(2) Molecular formula: $C_{19}H_{26}N_5O_4F$
(3) Mass spectrum (TSPMS): m/z 408 (M+H)$^+$
(4) Specific rotation: $[\alpha]_D^{25}$ −8° (c 0.4, DMSO-0.04 N HCl/H$_2$O=1:1)
(5) $^1$H NMR spectrum (400 MHz, DMSO-1 N DCl/D$_2$O= 5:1) δ (ppm): 1.68 (2H, m, piperidine), 1.84 (2H, quintet, tetrahydropyrimidine), 2.03 (2H, br d, piperidine), 3.06 (2H, br t, piperidine), 3.27 (4H, t, tetrahydropyrimidine), 3.48 (1H, dd, CONHCH$_2$), 3.53 (2H, br d, piperidine), 3.59 (1H, dd, CONHCH$_2$), 4.23 (1H, dd, CONHCH$_2$CH), 7.30 (1H, dd, C$_6$H$_3$), 7.64 (1H, br dd, C$_6$H$_3$), 7.67 (1H, br dd, C$_6$H$_3$)

Pharmacological Test Example 1: $\alpha_v\beta_3$ Binding Assay

Integrin $\alpha_v\beta_3$ antagonistic activity was first measured in a vitronectin-vitronectin receptor binding assay system in accordance with the method of Kouns et al. (W. C. Kouns, D. Kirchhofer, P. Hadvary, A. Edenhofer, T. Weller, G. Pfenninger, H. R. Baumgartner, L. K. Jennings and B. Steiner, Blood, 80, 2539–2547 (1992)). Specifically, a vitronectin receptor (protein content: 118 mg/ml) purified from the human placenta in accordance with the method of Pytela et al. (R. Pytela, M. D. Pierschbacher, S. Argraves, S. Suzuki, and E. Ruoslahti, Method in Enzymology, 144, 475–489 (1987)) was diluted 50 times with TBS (20 mM Tris-HCl, 150 mM NaCl, 1 mM CaCl$_2$, 1 mM MgCl$_2$, pH 7.4), and distributed and coated on wells (50 ml/well) of a plate (Maxisorp, Nunc, 96 well Immuno Plate). The plate was then allowed to stand at 4° C. for one day, washed twice with TBS (200 ml/well), and then subjected to blocking with TBS (150 ml/well) containing 1% bovine serum albumin (SIGMA) at 4° C. overnight. After washing twice with TBS (200 ml/well), 50 ml of vitronectin (CALBIOCHEM) adjusted to 0.2 mg/ml by the addition of TBS (TBS-Tween) containing 0.01% Tween-20 was mixed with 50 ml of each test compound adjusted to each concentration in wells, and a reaction was allowed to proceed at room temperature for 4 hr. After the completion of the reaction, the wells were washed five times with TBS-Tween. A solution prepared by diluting anti-vitronectin rabbit antiserum (CHEMICON) 500 times with TBS-Tween was added as a primary antibody in an amount of 50 ml/well, and a reaction was allowed to proceed at room temperature for 1.5 hr. After washing five times with 200 ml/well of TBS-Tween, a peroxidase (POD)-labeled anti-rabbit IgG antibody solution (CAPPEL) diluted 500 times with TBS-Tween was added as a secondary antibody in an amount of 50 ml/well, and a reaction was allowed to proceed at room temperature for 1.5 hr. After washing five times with TBS-Tween (200 ml/well), ABTS (2,2'-azino-bis(3-ethylbenzthiazoline-6-sulfonic acid), SIGMA) was adjusted to 1 mg/ml by the addition of a ten-fold diluted POD-buffer (ZYMED), and added in an amount of 50 ml/well, and a reaction was allowed to proceed for 5 to 10 min. A 0.1 M citric acid buffer (pH 4.3) containing 0.05% NaN$_3$ was added in an amount of 50 ml/well to stop the reaction, followed by the measurement of the absorbance at 415 nm with a microplate reader (MTP 32, Corona Electric) (reference: 675 nm). The total binding was defined as the absorbance after a reaction using 50 ml of TBS-Tween instead of the test compound, and the non-specific binding (100% inhibition) was defined as the absorbance after a reaction using 50 ml of TBS-Tween containing $2\times10^{-3}$ M RGDS. The inhibition was calculated by the following equation:

$$\text{Inhibition}(\%) = 100 - \frac{\{\text{absorbance in the presence of test compound} - \text{non-specific binding}\}}{(\text{total binding} - \text{non-specific binding})} \times 100$$

IC$_{50}$ was determined from a primary regression line of the logarithm of each concentration of the test compound and the logarithm of (100-inhibition)/inhibition.

The integrin $\alpha_v\beta_3$ antagonistic activity was 23 nM for the compound prepared in Example 6, and was 2.8 nM for the compound prepared in Example 14.

The dihydrochloride of the compound prepared in Example 6 and the dihydrochloride of the compound prepared in Example 14 were soluble in water (data omitted).

Pharmacological Test Example 2: GP IIb/IIIa Antagonistic Activity and Human Platelet Aggregation Inhibitory Activity GP IIb/IIIa antagonistic activity was measured for the compounds according to the present invention. The measurement of the GP IIb/IIIa antagonistic activity was carried out according to the method described in Pharmacological Test 2 in WO 94/21599. As a result, both the compounds prepared in Examples 6 and 14 had significant GP IIb/IIIa antagonistic activity, and the $IC_{50}$ values thereof were 4.8 nM and 12 nM, respectively.

Human platelet aggregation inhibitory activity was measured for the compounds according to the present invention. The measurement of the human platelet aggregation activity was carried out according to the method described in Pharmacological Test 1 in WO 94/21599. As a result, the compounds prepared in Examples 6 and 14 actually inhibited human platelet aggregation.

| | A | D | X | Z | p | q | $R^7$ | $R^8$ | Q | $R^9$ | J | $R^{10}$ | $R^{11}$ |
|---|---|---|---|---|---|---|---|---|---|---|---|---|---|
| 1 | pyrimidin-2-yl | Bond | N | N | 2 | 2 | m = 0 | n = 0 | >C=0 | H | Methylene | OH | tBu |
| 2 | pyrimidin-2-yl | Bond | N | N | 2 | 2 | m = 0 | n = 0 | >C=0 | H | Methylene | OH | H |
| 3 | pyrimidin-2-yl | >NH | CH | N | 2 | 2 | m = 0 | n = 0 | >C=0 | H | Methylene | OH | tBu |
| 4 | pyrimidin-2-yl | >NH | CH | N | 2 | 2 | m = 0 | n = 0 | >C=0 | H | Methylene | OtBu | tBu |
| 5 | pyrimidin-2-yl | >NH | CH | N | 2 | 2 | m = 0 | n = 0 | >C=0 | H | Methylene | OH | H |
| 6 | 1,4,5,6-tetrahydropyrimidin-2-yl | >NH | CH | N | 2 | 2 | m = 0 | n = 0 | >C=0 | H | Methylene | OH | H |
| 7 | 1,4,5,6-tetrahydropyrimidin-2-yl | >NH | CH | N | 2 | 2 | m = 0 | n = 0 | >C=0 | H | Methylene | OAc | H |
| 8 | pyrimidin-2-yl | >NH | CH | N | 2 | 2 | m = 0 | n = 0 | >C=0 | H | Ethylene | OtBu | OtBu |
| 9 | pyrimidin-2-yl | >NH | CH | N | 2 | 2 | m = 0 | n = 0 | >C=0 | H | Ethylene | OH | H |
| 10 | 1,4,5,6-tetrahydropyrimidin-2-yl | >NH | CH | N | 2 | 2 | m = 0 | n = 0 | >C=0 | H | Ethylene | OH | H |
| 11 | pyrimidin-2-yl | >NH | CH | N | 2 | 2 | m = 0 | n = 1 (3-F) | >C=0 | H | Methylene | OH | $CHPh_2$ |

-continued

| | A | D | X | Z | p | q | R⁷ | R⁸ | Q | R⁹ | J | R¹⁰ | R¹¹ |
|---|---|---|---|---|---|---|---|---|---|---|---|---|---|
| 12 | 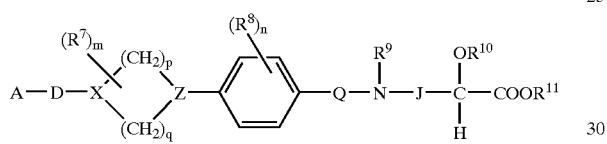 | >NH | CH | N | 2 | 2 | m = 0 | n = 1 (3-F) | >C = O | H | Methylene | OtBu | tBu |
| 13 | 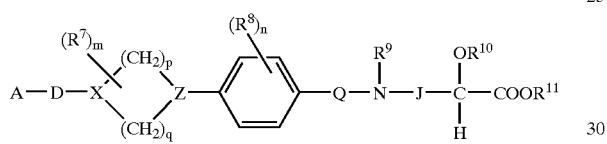 | >NH | CH | N | 2 | 2 | m = 0 | n = 1 (3-F) | >C = O | H | Methylene | OH | H |
| 14 | 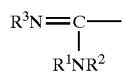 | >NH | CH | N | 2 | 2 | m = 0 | n = 1 (3-F) | >C = O | H | Methylene | OH | H |

What is claimed is:

1. A compound represented by formula (I) or a pharmaceutically acceptable salt or solvate thereof:

$$A-D-X\underset{(CH_2)_q}{\overset{(CH_2)_p}{\diagup\diagdown}}Z-\underset{(R^8)_n}{\overset{(R^7)_m}{\text{C}_6H_4}}-Q-\underset{H}{\overset{R^9}{N}}-J-\underset{H}{\overset{OR^{10}}{C}}-COOR^{11} \quad (I)$$

wherein

A represents a saturated or unsaturated five- to seven-membered heterocyclic group containing two nitrogen atoms, which is optionally condensed with another saturated or unsaturated five- to seven-membered carbocyclic ring or heterocyclic ring to form a bicyclic group, wherein the heterocyclic group and the bicyclic group are optionally substituted by $C_{1-6}$ alkyl, a halogen atom, amino, $C_{1-6}$ alkoxy, $C_{1-6}$ alkoxycarbonyl, or aralkyl and the $C_{1-6}$ alkyl, amino, $C_{1-6}$ alkoxy, $C_{1-6}$ alkoxycarbonyl, and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom, or a group represented by formula $$R^3N=\underset{R^1NR^2}{C-}$$

wherein $R^1$, $R^2$, and $R^3$, which may be the same or different, represent a hydrogen atom, $C_{1-6}$ alkyl, $C_{2-6}$ alkenyl, $C_{2-6}$ alkynyl, aralkyl, or nitrile, or $R^1$ and $R^2$ may together form group $—(CH_2)_i—$, wherein i is 4 or 5, or group $—(CH_2)_2—O—(CH_2)_2—$, and the $C_{1-6}$ alkyl, $C_{2-6}$ alkenyl, $C_{2-6}$ alkynyl, and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom;

D represents a bond; $>NR^4$ wherein $R^4$ represents a hydrogen atom or $C_{1-6}$ alkyl and this alkyl group is optionally substituted by phenyl optionally substituted by $C_{1-6}$ alkoxy, $C_{1-6}$ alkyl, $C_{1-6}$ alkoxy, $C_{1-6}$ alkoxycarbonyl, aralkyl, amino, hydroxyl, or a halogen atom; $>CR^5R^6$ wherein $R^5$ and $R^6$ each independently represent a hydrogen atom or $C_{1-6}$ alkyl and this alkyl group is optionally substituted by phenyl optionally substituted by $C_{1-6}$ alkoxy, $C_{1-6}$ alkyl, $C_{1-6}$ alkoxy, $C_{1-6}$ alkoxycarbonyl, aralkyl, amino, hydroxyl, or a halogen atom; $—O—$; or $—S—$;

one of X and Z is CH and the other is N;

$R^7$ represents $C_{1-6}$ alkyl, $C_{1-6}$ alkoxy, a halogen atom, amino, nitro, hydroxyl, oxo, or cyano and the $C_{1-6}$ alkyl and $C_{1-6}$ alkoxy groups are optionally substituted by $C_{1-6}$ alkyl, $C_{1-6}$ alkoxy, $C_{1-6}$ alkoxycarbonyl, aralkyl, amino, hydroxyl, or a halogen atom;

$R^8$ represents $C_{1-6}$ alkyl, $C_{1-6}$ alkoxy, a halogen atom, amino optionally substituted by one or two $C_{1-6}$ alkyl groups, nitro, hydroxyl, oxo, or cyano and the $C_{1-6}$ alkyl and $C_{1-6}$ alkoxy groups are optionally substituted by $C_{1-6}$ alkyl, $C_{1-6}$ alkoxy, $C_{1-6}$ alkoxycarbonyl, aralkyl, amino, hydroxyl, or a halogen atom;

Q represents $>C=O$, $>CHR^{13}$, or $>CHOR^{13}$ wherein $R^{13}$ represents a hydrogen atom or $C_{1-6}$ alkyl;

$R^9$ represents a hydrogen atom, $C_{1-6}$ alkyl, $C_{2-6}$ alkenyl, $C_{2-6}$ alkynyl, or aralkyl and the $C_{1-6}$ alkyl, $C_{2-6}$ alkenyl, $C_{2-6}$ alkynyl, and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom;

J represents a bond or alkylene having 1 to 3 carbon atoms wherein alkylene is optionally substituted by $C_{1-6}$ alkyl, $C_{1-6}$ alkoxy, $C_{1-6}$ alkoxycarbonyl, aralkyl, amino, hydroxyl, or a halogen atom;

$R^{10}$ represents a hydrogen atom, $C_{1-6}$ alkyl, $C_{2-6}$ alkenyl, $C_{2-6}$ alkynyl, aralkyl, or acetyl and the $C_{1-6}$ alkyl, $C_{2-6}$ alkenyl, $C_{2-6}$ alkynyl, aralkyl, and acetyl groups are optionally substituted by $C_{1-6}$ alkyl, $C_{1-6}$ alkoxy, $C_{1-6}$ alkoxycarbonyl, aralkyl, amino, hydroxyl, or a halogen atom;

$R^{11}$ represents a hydrogen atom, $C_{1-6}$ alkyl, or aralkyl and the $C_{1-6}$ alkyl and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom;

m is an integer of 0 to 5;

n is an integer of 0 to 4;

p is an integer of 1 to 3;

q is an integer of 1 to 3; and the sum of p and g is 4.

2. The compound according to claim 1, wherein X represents CH and Z represents N.

3. The compound according to claim 1, wherein A represents a group of formula

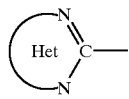

wherein
Het represents a saturated or unsaturated five- to seven-membered heterocyclic group containing two nitrogen atoms, which is optionally condensed with another saturated or unsaturated five- to seven-membered carbocyclic ring or heterocyclic ring to form a bicyclic group, wherein the heterocyclic group and the bicyclic group are optionally substituted by $C_{1-6}$ alkyl, amino, $C_{1-6}$ alkoxy, $C_{1-6}$ alkoxycarbonyl, or aralkyl and the $C_{1-6}$ alkyl, amino, $C_{1-6}$ alkoxy, $C_{1-6}$ alkoxycarbonyl, and aralkyl groups are optionally substituted by $C_{1-6}$ alkyl, $C_{1-6}$ alkoxy, $C_{1-6}$ alkoxycarbonyl, aralkyl, amino, hydroxyl, or a halogen atom.

4. The compound according to claim 1, wherein A represents a group of formula

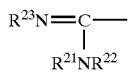

wherein
$R^{21}$ and $R^{23}$, which may be the same or different, represent a hydrogen atom, $C_{1-6}$ alkyl, $C_{2-6}$ alkenyl, or aralkyl
$R^{22}$ represents a hydrogen atom or $C_{1-6}$ alkyl, or
$R^{21}$ and $R^{23}$ may together form
group —(CH$_2$)$_4$—,
group —(CH$_2$)$_3$—,
group —CHR$^{24}$CH$_2$CH$_2$— wherein $R^{24}$ represents $C_{1-6}$ alkyl, a halogen atom, or amino, the alkyl group is optionally substituted by $C_{1-6}$ alkyl, $C_{1-6}$ alkoxy, $C_{1-6}$ alkoxycarbonyl, aralkyl, amino, hydroxyl, or a halogen atom, and the amino group is optionally substituted by $C_{1-6}$ alkyl, $C_{1-6}$ alkoxy, $C_{1-6}$ alkoxycarbonyl, or aralkyl,
group —CH$_2$CHR$^{24}$CH$_2$— wherein $R^{24}$ is as defined above,
group —CH$_2$CH$_2$—,
group —CHR$^{24}$CH$_2$— wherein $R^{24}$ is as defined above,
group —CR$^{25}$=CR$^{26}$— wherein $R^{25}$ and $R^{26}$, which may be the same or different, represent a hydrogen atom or $C_{1-6}$ alkyl, or $R^{25}$ and $R^{26}$ may together form —CH=CH—CH=CH—, —CR$^{24}$=CH—CH=CH— wherein $R^{24}$ is as defined above, —CH=CR$^{24}$—CH=CH— wherein $R^{24}$ is as defined above, —N=CH—CH=CH—, or —CH=N—CH=CH—, or
$R^{21}$ and $R^{23}$ may together form
=CH—CH=CH—,
=CR$^{24}$—CH=CH—,
=CH—CR$^{24}$=CH—,
=CH—CH=N—, or
=CH—N=CH—, and
$R^{22}$ may represent a single bond between $R^{21}$ and the nitrogen atom attached to $R^{21}$.

5. The compound according to claim 1, wherein D represents a bond or >NR$^4$.

6. The compound according to claim 1, wherein Q represents >C=O or >CH$_2$.

7. The compound according to claim 1, wherein J represents an optionally substituted methylene or ethylene chain.

8. The compound according to claim 1, wherein m and n are each an integer of 0 to 2.

9. The compound according to claim 1, wherein p and q are each 2.

10. The compound according to claim 1, wherein A represents a group of formula

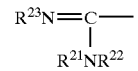

wherein
$R^{21}$ and $R^{23}$, which may be the same or different, represent a hydrogen atom, $C_{1-6}$ alkyl, $C_{2-6}$ alkenyl, or aralkyl
$R^{22}$ represents a hydrogen atom or $C_{1-6}$ alkyl, or
$R^{21}$ and $R^{23}$ may together form
group —(CH$_2$)$_4$—,
group —(CH$_2$)$_3$—,
group —CHR$^{24}$CH$_2$CH$_2$— wherein $R^{24}$ represents $C_{1-6}$ alkyl, a halogen atom, or amino, the alkyl group is optionally substituted by $C_{1-6}$ alkyl, $C_{1-6}$ alkoxy, $C_{1-6}$ alkoxycarbonyl, aralkyl, amino, hydroxyl, or a halogen atom, and the amino group is optionally substituted by $C_{1-6}$ alkyl, $C_{1-6}$ alkoxy, $C_{1-6}$ alkoxycarbonyl, or aralkyl,
group —CH$_2$CHR$^{24}$CH$_2$— wherein $R^{24}$ is as defined above,
group —CH$_2$CH$_2$—,
group —CHR$^{24}$CH$_2$— wherein $R^{24}$ is as defined above,
group —CR$^{25}$=CR$^{26}$— wherein $R^{25}$ and $R^{26}$, which may be the same or different, represent a hydrogen atom or $C_{1-6}$ alkyl, or $R^{25}$ and $R^{26}$ may together form —CH=CH—CH=CH—, —CR$^{24}$=CH—CH=CH— wherein $R^{24}$ is as defined above, —CH=CR$^{24}$—CH=CH— wherein $R^{24}$ is as defined above, —N=CH—CH=CH—, or —CH=N—CH=CH—, or
$R^{21}$ and $R^{23}$ may together form
=CH—CH=CH—,
=CR$^{24}$—CH=CH—,
=CH—CR$^{24}$=CH—,
=CH—CH=N—, or
=CH—N=CH—, and
$R^{22}$ may represent a single bond between $R^{21}$ and the nitrogen atom attached to $R^{21}$;
D represents a bond or >NR$^4$;
X represents CH;
Z represents N;
Q represents >C=O or >CH$_2$;
m and n are each an integer of 0 or 1;
$R^7$ represents optionally substituted $C_{1-6}$ alkyl, a halogen atom, or oxo;
$R^8$ represents a halogen atom, nitro, optionally substituted amino, cyano, optionally substituted $C_{1-6}$ alkyl, or optionally substituted $C_{1-6}$ alkoxy;
$R^9$ represents a hydrogen atom, optionally substituted $C_{1-6}$ alkyl, or optionally substituted aralkyl;

J represents an optionally substituted methylene or ethylene chain;

$R^{10}$ represents a hydrogen atom, optionally substituted $C_{1-6}$ alkyl, optionally substituted $C_{2-6}$ alkenyl, optionally substituted aralkyl, or optionally substituted acetyl;

$R^{11}$ represents a hydrogen atom, optionally substituted $C_{1-6}$ alkyl, or optionally substituted aralkyl; and the sum of p and q is 4.

11. The compound according to claim 1, which is selected from the group consisting of:

t-butyl(2S)-hydroxy-3-[4-{4-(pyrimidin-2-yl)piperazin-1-yl}benzoylamino]propionate;
(2S)-hydroxy-3-[4-{4-(pyrimidin-2-yl)piperazin-1-yl}benzoylamino]propionic acid;
t-butyl(2S)-hydroxy-3-[4-{4-(pyrimidin-2-ylamino)piperidin-1-yl}benzoylamino]propionate;
t-butyl(2S)-t-butoxy-3-[4-{4-(pyrimidin-2-ylamino)piperidin-1-yl}benzoylamino]propionate;
(2S)-hydroxy-3-[4-{4-(pyrimidin-2-ylamino)piperidin-1-yl}benzoylamino]propionic acid;
(2S)-hydroxy-3-[4-{4-(1,4,5,6-tetrahydropyrimidin-2-ylamino)piperidin-1-yl}benzoylamino]propionic acid;
(2S)-acetoxy-3-[4-{4-(1,4,5,6-tetrahydropyrimidin-2-ylamino)piperidin-1-yl}benzoylamino]propionic acid;
t-butyl(2S)-t-butoxy-4-[4-{4-(pyrimidin-2-ylamino)piperidin-1-yl}benzoylamino]butyrate;
(2S)-hydroxy-4-[4-{4-(pyrimidin-2-ylamino)piperidin-1-yl}benzoylamino]butyric acid;
(2S)-hydroxy-4-[4-{4-(1,4,5,6-tetrahydropyrimidin-2-ylamino)piperidin-1-yl}benzoylamino]butyric acid;
benzhydryl 3-[3-fluoro-4-{4-(pyrimidin-2-ylamino)piperidin-1-yl}benzoylamino]-(2S)-hydroxy-propionate;
t-butyl(2S)-t-butoxy-3-[3-fluoro-4-{4-(pyrimidin-2-ylamino)piperidin-1-yl}benzoylamino]propionate;
3-[3-fluoro-4-{4-(pyrimidin-2-ylamino)piperidin-1-yl}benzoylamino]-(2S)-hydroxypropionic acid; and
3-[3-fluoro-4-{4-(1,4,5,6-tetrahydropyrimidin-2-ylamino)piperidin-1-yl}benzoylamino]-(2S)-hydroxy-propionic acid.

12. A pharmaceutical composition comprising as active ingredient the compound according to claim 1 or a pharmaceutically acceptable salt or solvate thereof.

13. A process for producing the compound according to claim 1, comprising the step of reacting a compound of formula (II')

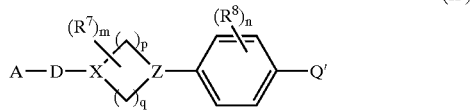

(II')

wherein A, D, X, Z, $R^7$, $R^8$, m, n, p, and q are as defined in claim 1; and Q' represents —COOH or —CHO, or a salt thereof, with a compound of formula (III)

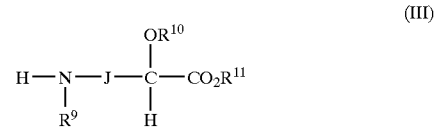

(III)

wherein J, $R^9$, $R^{10}$, and $R^{11}$ are as defined in claim 1.

14. A method for treating $\alpha_v\beta_3$-mediated disease selected from the group consisting of acute myocardial infarction, neointima formation hypertrophy, restenosis after PTCA/stent operation, unstable angina, arteria coronary syndrome, angina pectoris after PTCA/stent operation, and arterial sclerosis, which comprises the step of administering an effective amount of the compound according to claim 1 or a pharmaceutically acceptable salt or solvate thereof, together with a pharmaceutically acceptable carrier, to a mammal including a human.

15. A method for treating diseases where GP IIb/IIIa antagonistic activity and/or platelet aggregation inhibitory activity are therapeutically effective, which comprises the step of administering an effective amount of the compound according to claim 1 or a pharmaceutically acceptable salt or solvate thereof, together with a pharmaceutically acceptable carrier, to a mammal including a human.

16. A method for the treatment of platelet thrombosis or thromboembolism, the improvement of peripheral circulating blood stream, the inhibition of blood clotting during extracorporeal circulation, or the treatment of thrombotic thrombocytopenic purpura or hemolytic uremic syndrome, which comprises the step of administering an effective amount of the compound according to claim 1 or a pharmaceutically acceptable salt or solvate thereof, together with a pharmaceutically acceptable carrier, to a mammal including a human.

17. A method for inhibiting platelet aggregation, which comprises the step of administering an effective amount of the compound according to claim 1 or a pharmaceutically acceptable salt or solvate thereof, together with a pharmaceutically acceptable carrier, to a mammal including a human.

* * * * *